(12) United States Patent
Gygi et al.

(10) Patent No.: US 8,618,248 B2
(45) Date of Patent: Dec. 31, 2013

(54) PHOSPHOPEPTIDE COMPOSITIONS AND ANTI-PHOSPHOPEPTIDE ANTIBODY COMPOSITIONS AND METHODS OF DETECTING PHOSPHORYLATED PEPTIDES

(75) Inventors: Steven P. Gygi, Foxborough, MA (US); Judit Villen, Boston, MA (US); Sean Beausoleil, Merrimack, NH (US)

(73) Assignee: President and Fellows of Harvard College, Cambridge, MA (US)

( * ) Notice: Subject to any disclaimer, the term of this patent is extended or adjusted under 35 U.S.C. 154(b) by 1395 days.

(21) Appl. No.: 11/980,279

(22) Filed: Oct. 30, 2007

(65) Prior Publication Data

US 2008/0214782 A1     Sep. 4, 2008

Related U.S. Application Data

(60) Provisional application No. 60/855,664, filed on Oct. 31, 2006.

(51) Int. Cl.
| | | |
|---|---|---|
| *C07K 7/08* | (2006.01) | |
| *C07K 5/10* | (2006.01) | |
| *C07K 7/06* | (2006.01) | |
| *C07K 16/18* | (2006.01) | |

(52) U.S. Cl.
CPC ........................................ *C07K 7/08* (2013.01)
USPC ........... 530/326; 530/330; 530/329; 530/327; 530/300; 530/389.1

(58) Field of Classification Search
None
See application file for complete search history.

(56) References Cited

U.S. PATENT DOCUMENTS

| | | | |
|---|---|---|---|
| 4,439,196 A | 3/1984 | Higuchi | |
| 4,447,224 A | 5/1984 | DeCant et al. | |
| 4,447,233 A | 5/1984 | Mayfield | |
| 4,475,196 A | 10/1984 | LaZor | |
| 4,486,194 A | 12/1984 | Ferrara | |
| 4,487,603 A | 12/1984 | Harris | |
| 4,522,811 A | 6/1985 | Eppstein et al. | |
| 4,596,556 A | 6/1986 | Morrow et al. | |
| 4,790,824 A | 12/1988 | Morrow et al. | |
| 4,881,175 A | 11/1989 | Ladner | |
| 4,941,880 A | 7/1990 | Burns | |
| 4,946,778 A | 8/1990 | Ladner et al. | |
| 4,954,617 A | 9/1990 | Fanger et al. | |
| 5,013,653 A | 5/1991 | Huston et al. | |
| 5,064,413 A | 11/1991 | McKinnon et al. | |
| 5,091,513 A | 2/1992 | Huston et al. | |
| 5,132,405 A | 7/1992 | Huston et al. | |
| 5,143,854 A | 9/1992 | Pirrung et al. | |
| 5,225,539 A | 7/1993 | Winter | |
| 5,258,498 A | 11/1993 | Huston et al. | |
| 5,260,203 A | 11/1993 | Ladner et al. | |
| 5,312,335 A | 5/1994 | McKinnon et al. | |
| 5,374,548 A | 12/1994 | Caras | |
| 5,383,851 A | 1/1995 | McKinnon et al. | |
| 5,399,163 A | 3/1995 | Peterson et al. | |
| 5,399,331 A | 3/1995 | Loughrey et al. | |
| 5,416,016 A | 5/1995 | Low et al. | |
| 5,434,049 A | 7/1995 | Okano et al. | |
| 5,455,030 A | 10/1995 | Ladner et al. | |
| 5,476,786 A | 12/1995 | Huston | |
| 5,482,858 A | 1/1996 | Huston et al. | |
| 5,530,101 A | 6/1996 | Queen et al. | |
| 5,556,752 A | 9/1996 | Lockhart et al. | |
| 5,585,089 A | 12/1996 | Queen et al. | |
| 5,624,821 A | 4/1997 | Winter et al. | |
| 5,632,957 A | 5/1997 | Heller et al. | |
| 5,648,260 A | 7/1997 | Winter et al. | |
| 5,677,425 A | 10/1997 | Bodmer et al. | |
| 5,693,762 A | 12/1997 | Queen et al. | |
| 5,700,637 A | 12/1997 | Southern | |
| 5,714,350 A | 2/1998 | Co et al. | |
| 5,744,305 A | 4/1998 | Fodor et al. | |
| 5,770,456 A | 6/1998 | Holmes | |
| 5,800,992 A | 9/1998 | Fodor et al. | |
| 5,807,522 A | 9/1998 | Brown et al. | |
| 5,830,645 A | 11/1998 | Pinkel et al. | |
| 5,856,174 A | 1/1999 | Lipshutz et al. | |
| 5,869,046 A | 2/1999 | Presta et al. | |
| 5,959,098 A | 9/1999 | Goldberg et al. | |
| 5,965,452 A | 10/1999 | Kovacs | |
| 6,013,440 A | 1/2000 | Lipshutz et al. | |
| 6,022,963 A | 2/2000 | McGall et al. | |
| 6,045,996 A | 4/2000 | Cronin et al. | |
| 6,048,695 A | 4/2000 | Bradley et al. | |

(Continued)

FOREIGN PATENT DOCUMENTS

| | | |
|---|---|---|
| EP | 0 154 316 | 9/1985 |
| EP | 0 401 384 | 12/1990 |

(Continued)

OTHER PUBLICATIONS

Jensen ('Automated phosphorylation site mapping' Nature Biotech v24 Oct. 2006 pp. 1226-1227).*
Ballif et al (Molecular and Cellular Proteomics 'Phosphoproteomic analysis of the developing mouse brain' v3 pp. 1093-1101), (2004).*
Alessi et al. "Molecular basis for the substrate specificity of protein kinase B; comparison with MAPKAP kinase-1 and p70 S6 kinase," FEBS Letters, Dec. 16, 1996, vol. 399, iss 3, pp. 333-338; Published by Elsevier BV on behalf of the Federation of European Biochemical Societies.
Allen "Ligand-Targeted Therapeutics in Anticancer Therapy," Nat Canc Rev, Oct. 2002, vol. 2, pp. 750-763; doi:10.1038/nrc903.
Altschul et al. "Basic Local Alignment Search Tool," J Mol Biol, Oct. 5, 1990, vol. 215, iss 3, pp. 403-410; doi: 10.1016/S0022-2836(05)80360-2.
Altschul et al. "Gapped BLAST and PSI-BLAST: a new generation of protein database search programs," Nucl Acid Res, Sep. 1997, vol. 25, No. 17, pp. 3389-3402; doi:10.1093/nar/25.17.3389.

(Continued)

*Primary Examiner* — Karlheinz R Skowronek
*Assistant Examiner* — Mindy Newman
(74) *Attorney, Agent, or Firm* — Lawson & Weitzen LLP; Sonia K. Guterman; Teofilo Javier, Jr.

(57) ABSTRACT

The present invention relates to phosphopeptide compositions and anti-phosphopeptide antibody compositions. Also provided are methods of identifying phosphorylation sites in phosphorylated peptides and phosphorylation site motifs.

19 Claims, 10 Drawing Sheets

(56) References Cited

U.S. PATENT DOCUMENTS

| | | | |
|---|---|---|---|
| 6,054,270 | A | 4/2000 | Southern |
| 6,063,338 | A | 5/2000 | Pham et al. |
| 6,121,022 | A | 9/2000 | Presta et al. |
| 6,165,745 | A | 12/2000 | Ward et al. |
| 6,180,370 | B1 | 1/2001 | Queen et al. |
| 6,194,551 | B1 | 2/2001 | Idudogie |
| 6,258,606 | B1 | 7/2001 | Kovacs |
| 6,261,776 | B1 | 7/2001 | Pirrung et al. |
| 6,277,375 | B1 | 8/2001 | Ward |
| 6,277,489 | B1 | 8/2001 | Abbot et al. |
| 6,277,628 | B1 | 8/2001 | Johann et al. |
| 6,350,861 | B1 | 2/2002 | Co et al. |
| 6,358,201 | B1 * | 3/2002 | Childre et al. ............... 600/300 |
| 2001/0008765 | A1 | 7/2001 | Shinoki et al. |
| 2001/0012537 | A1 | 8/2001 | Anderson et al. |
| 2001/0014448 | A1 | 8/2001 | Chappa et al. |
| 2001/0014449 | A1 | 8/2001 | Nerenberg et al. |
| 2001/0016322 | A1 | 8/2001 | Caren et al. |
| 2001/0018642 | A1 | 8/2001 | Balaban et al. |
| 2001/0019827 | A1 | 9/2001 | Dawson et al. |
| 2003/0153043 | A1 | 8/2003 | Carr et al. |

FOREIGN PATENT DOCUMENTS

| | | |
|---|---|---|
| EP | 1176195 | 1/2002 |
| WO | WO 88/00052 | 1/1988 |
| WO | WO 94/10332 | 5/1994 |
| WO | WO 94/29351 | 12/1994 |
| WO | WO 96/17958 | 6/1996 |
| WO | WO 97/46313 | 12/1997 |
| WO | WO 98/24884 | 6/1998 |
| WO | WO 99/09217 | 2/1999 |
| WO | WO 99/51773 | 10/1999 |
| WO | WO 99/54342 | 10/1999 |
| WO | WO 00/42072 | 7/2000 |
| WO | WO 01/14424 | 3/2001 |
| WO | WO 02/092780 | 11/2002 |
| WO | WO 03/035835 | 5/2003 |
| WO | WO 03/074679 | 9/2003 |

OTHER PUBLICATIONS

Bakalarski et al. "The effects of mass accuracy, data acquisition speed, and search algorithm choice on peptide identification rates in phosphoproteomics," Anal Bioanal Chem, Sep. 14, 2007, vol. 389, pp. 1409-1419; doi: 10.1007/s00216-007-1563-x.

Ballif et al. "Phosphoproteomic Analysis of the Developing Mouse Brain," Mol Cell Proteom, Sep. 2, 2004, vol , pp. 1093-1101; doi:10. 1074/mcp.M400085-MCP200.

Ballif et al. "Idenification of 14-3-3e Substrates from Embryonic Murine Brain," J Proteom Res, Aug. 2, 2006, vol. 5, pp. 2372-2379; doi: 10.1021/pr060206k.

Beausoleil et al. "Large-scale characterization of HeLa cell nuclear phosphoproteins," Pro Natl Sci Acad, Aug. 17, 2004, vol. 101, No. 33, pp. 12130-121235; doi: 10.1073/pnas.0404720101.

Beausoleil et al. "A probability-based approach for high-throughput protein phosphorylation analysis and site localization," Nat Biotech, Oct. 2006, vol. 24, No. 10, pp. 1285-1292; doi: 10.1038/nbt1240.

Berge et al. "Pharmaceutical Salts," J Pharmaceut Sci, Jan. 1977, vol. 66, No. 1, pp. 1-19; Doi: 10.1002/jps.2600660104.

Bird et al. "Single-Chain Antigen-Binding Proteins," Science, Oct. 21, 1988, vol. 4877, pp. 423-426; DOI: 10.1126/science.3140379.

Bloemen et al. "Adhesion molecules: a new target for immunoliposome-mediated drug delivery," FEBS Lett, Jan. 3, 1995, vol. 357, iss 2, pp. 140-144; Published by Elsevier BV on behalf of the Federation of European Biochemical Societies.

Bowtell "Options available—from start to finish—for obtaining expression data by microarray" Nat Genet, Jan. 1999, vol. 21, suppl, pp. 25-32; doi:10.1038/4455.

Brennan et al. "Preparation of Bispecific Antibodies by Chemical Recombination of Monoclonal Immunoglobin G1 Fragments" Science, Jul. 5, 1985, vol. 229, pp. 81-83; doi: 10.1126/science.3925553.

Briscoe et al. "Delivery of superoxide dismutase to pulmonary epithelium via pH-sensitive liposomes," Am J Physiol Lung Cell Mol Physiol, Mar. 1995, vol. 268, pp. L374-L380; The American Physiological Society.

Cohen "The regulation of protein function by multisite phosphorylation—a 25 year update," Trends in Biochem Sci, Dec. 2000, vol. 25, pp. 595-601; doi: 10.1016/S0968-0004(00)01712-6.

Cox et al. "A directory of human germ-line Vx segments reveals a strong bias in their usage," Eur J Immunol, Apr. 1994, vol. 24, iss 4, pp. 827-836; doi: 10.1002/eji.1830240409.

Crooks et al. "WebLogo: A Sequence Logo Generator," Genome Res, Jun. 2004, vol. 14, pp. 1188-1190; doi: 10.1101/gr.849004.

Diella et al. "Phospho.ELM: A Database of experimentally verified phosphorylation sites in eukaryotic proteins," BMC Bioinformatics, Jun. 22, 2004, vol. 5, iss 79; doi: 10.1186/1471-2105-5-79.

Du et al. "TRB3: A tribbles Homolog That Inhibits Akt/PKB Activation by Insulin in Liver," Science, Jun. 6, 2003, vol. 300, iss 5625, pp. 1574-1577; doi: 10.1126/science.1079817.

Elias et al. "Comparative evaluation of mass spectrometry platforms used in large-scale proteomics investigations," Nat Method, Sep. 2005, vol. 2, No. 9, pp. 667-675; doi:10.1038/nmeth785.

Elias et al. "Target-decoy search strategy for increased confidence in large-scale protein identification by mass spectrometry," Nat Method, Mar. 2007, vol. 4, No. 3, pp. 207-214; doi: 10.1038/NMETH1019.

Ficarro et al. "Phosphoproteome analysis by mass spectrometry and its application to *Saccharomyces cerevisiae*," Nat Biotechnol, Mar. 2002, vol. 20, pp. 301-305; Nature Publishing Group.

Filder & Killon "Systematic Targeting of Liposome-Encapsulated Immunomodulations to Macrophages for Treatment of Cancer Metastasis," Immunomethod, Jun. 1994, vol. 4, iss 3, pp. 273-279; doi:10.1006/immu.1994.1029.

Fishwild et al. "High-avidity human IgGk monoclonal antibodies from a novel strain of minilocus transgenic mice," Nat Biotechnol, Jul. 1996, vol. 14, 845-851; doi:10.1038/nbt0796-845.

Glennie et al. "Preparation and performance of bispecific F(ab'y)2 antibody containing thioether-linked Fab'y fragments," J Immunol, Oct. 1, 1987, vol. 139, No. 7, pp. 2367-2375; Published by The American Association of Immunologists, Inc.

Graziano et al. "Construction and Characterization of a Humanized Anti-y-Ig Receptor Type I (FcyRI) Monoclonal Antibody," J Immunol, Nov. 1995, vol. 155, pp. 4996-5002; Published by The American Association of Immunologists, Inc.

Gruhler et al. "Quantitative Phosphoproteomics Applied to the Yeast Pheromone Signaling Pathway," Mol Cellul Proteom, Jan. 22, 2005, vol. 4, pp. 310-327; doi: 10.1074/mcp.M400219-MCP200.

Haas et al. "Optimization and Use of Peptide Mass Measurement Accuracy in Shotgun Proteomics," Mol Cellul Proteom, Apr. 23, 2006, vol, pp. 1326-1337; doi: 10.1074/mcp.M500339-MCP200.

Hornbeck et al. "PhosphoSite: A bioinformatics resource dedicated to physiological protein phosphorylation," Proteomics, Jun. 2004, vol. 4, pp. 1551-1561; doi: 10.1002/pmic.200300772.

Hunter et al. "Signaling—2000 and Beyond," Cell, Jan. 7, 2000, vol. 100, pp. 113-127; doi:10.1016/S0092-8674(00)81688-8.

Huston et al. "Protein engineering of antibody binding sites: Recovery of specific activity in an anti-digoxin single-chain Fv analogue produced in *Escherichia coli*," Proc Natl Acad Sci, USA, Aug. 1988, vol. 85, pp. 5879-5883; National Academy of Sciences.

Jin et al. "Phosphoproteome analysis of mouse liver using immobilized metal affinity purification and linear ion trap mass spectrometry," Rapid Commun in Mass Spectrometry, Sep. 2004, vol. 18, iss 18, pp. 2169-2176; doi: 10.1002/rcm.1604.

Johnston, "Gene chips: Array of hope for understanding gene regulation," Curr Biol, Feb. 1998, vol. 8, iss 5, R171-R174; doi:10.1016/S0960-9822(98)70103-4.

Jones, "Replacing the complementarity-determining regions in a human anitbody with those from a mouse," Nature, May 29, 1986, vol. 321, pp. 522-525 ; doi:10.1038/321522a0.

Karpovsky et al., "Production of Target-Specific Effector Cells Using Hetero-Cross-Linked Aggregates Containing Anit-Target Cell and Anti-Fcy Receptor Antibodies," J Experiment Med, Dec. 1984, vol. 160, No. 6, pp. 1686-1701 doi:10.1084/jem.160.6.1686.

(56) References Cited

OTHER PUBLICATIONS

Kern et al. "Direct Hybridization of Large-Insert Genomic Clones on High-Density Gridded cDNA Filter Arrays," BioTechniques, Jul. 1997, vol. 23, No. 1, pp. 120-124; Informa BioSciences, New York, New York.

Keinanen et al., "Biosynthetic lipid-tagging of antibodies," FEBS Letters, Jun. 6, 1994 vol. 346, iss 1, pp. 123-126; doi:10.1016/0014-5793(94)00313-0.

Li et al. "Large-Scale Phosphorylation Analysis of Factor-Arrested *Saccharomyces cerevisiae*," J Proteome Res, Jan. 17, 2007, vol. 6, pp. 1190-1197; doi: 10.1021/pr060559j.

Liu et al. "Heteroantibody duplexes target cells for lysis by cytotoxic T lymphocytes," Proc Natl Acad Sci USA, Dec. 1985, vol. 82, pp. 8648-8652; National Academy of Sciences.

Lonberg et al. "Antigen-specific human antibodies from mice comprising four distinct genetic modifications," Nature, Apr. 28, 1994, vol. 368, pp. 856-859; doi:10.1038/368856a0.

Manceau et al. "Major phosphorylation of SF1 on adjacent Ser-Pro motifs enhances interaction with U2AF," FEBS J, Feb. 2006, vol. 273, iss 3, pp. 577-587; doi: 10.1111/j.1742-4658.2005.05091.x.

Mesli et al. "Distribution of the lipolysis stimulated receptor in adult and embryonic murine tissues and lethality of LSR-/- embryos at 12.5 to 14.5 days of gestation," Eur J Biochem, Jul. 6, 2004, vol. 271, pp. 3103-3114; doi: 10.1111/j.1432-1033.2004.04223.x.

Monteiro et al. "Molecular Heterogeneity of Fc Receptors Detected by Receptor-Specific Monoclonal Antibodies," J Immunol, Mar. 15, 1992, vol. 148, pp. 1764-1770; The American Association of Immunologists.

Morton et al. "Structure and Function of Human IgA Fc Receptors (FcAlphaR)," Critc Rev Immunol, 1996, vol. 16, pp. 423-440; Begell House, Inc.

Moser et al. "Phosphoproteomic Analysis of Rat Liver by High Capacity IMAC and LC-MS/MS," J Proteome Res, Dec. 1, 2005, vol. 5, pp. 98-104; doi: 10.1021/pr0503073.

Myers et al. "Optimal alignments in linear space," Comput Appl Biosci, 1988, vol. 4, iss 1, pp. 11-17; doi: 10.1093/bioinformatics/4.1.11.

Needleman et al. "A General Method Applicable to the Search for Similarities in the Amino Acid Sequence of Two Proteins," J Mol Biol, Mar. 28, 1970, vol. 48, pp. 443-453; doi:10.1016/0022-2836(70)90057-4.

Oda et al. "Enrichment analysis of phosphorylated proteins as a tool for probing the phosphoproteome," Nature Biotech, Apr. 2001, vol. 19, pp. 379-382; doi:10.1038/86783.

Owais et al. "Cholorquine Encapsulated in Malaria-Infected Erythrocyte-Specific Antibody-Bearing Liposomes Effectively Controls Choloroquine-Resistant *Plasmodium berghei* Infections in Mice," Antimicrob Agent Chemother, Jan. 1995, vol. 39, No. 1, pp. 180-184; http://aac.asm.org/cgi/content/abstract/39/1/180.

Pastan et al. "Overview:Immunotoxins in cancer therapy," Curr Opin Investig Drug, Jul. 2002, vol. 3, iss 7, pp. 1089-1091; PharmaPress Ltd.

Pawson et al. "Protein phosphorylation in signaling—50 years and counting," Trend Biochem Sci, Jun. 2005, vol. 30, iss 6, pp. 286-290; doi: 10.1016/j.tibs.2005.04.013.

Payne "Progress in immunoconjugate cancer therapeutics," Cancer Cell, Mar. 2003, vol. 3, pp. 207-212; doi:10.1016/S1535-6108(03)00057-6.

Peng et al. "Evaluation of Multidimensional Chromatography Coupled with Tandem Mass Spectrometry (LC/LC-MS/MS) for Large-Scale Protein Analysis: The Yeast Proteome," J Proteome Res, Oct. 15, 2002, vol. 2, pp. 43-50; doi: 10.1021/pr025556v.

Peri et al. "Human protein reference database as a discovery resource for proteomics," Nucl Acid Res, 2004, vol. 32, pp. D497-D501; doi:10.1093/nar/gkh070.

Queen et al. "A humanized antibody that binds to the interleukin 2 receptor," Proc Natl Acad Sci, USA, vol. 86, pp. 10029-10033; National Academy of Sciences, (Dec. 1989).

Ranade "Drug Delivery Systems. 1. Site-Specific Drug Delivery Using Liposomes as Carriers," J Clin Pharmacol, Aug. 1, 1989, vol. 29, pp. 685-694; American College of Clinical Pharmacology, Inc.

Rappsilber et al. "Stop and Go Extraction Tips for Matrix-Assisted Laser Desorption/Ionization, Nanoelectrospray, and LC/MS Sample Pretreatment in Protemics," Anal Chem, Feb. 2003, vol. 75, pp. 663-670; doi: 10.1021/ac026117i.

Riechmann et al. "Reshaping human anitbodies for therapy," Nature, Mar. 24, 1988, vol. 332, pp. 323-327; doi:10.1038/332323a0.

Rigaut et al. "A generic protein purification method for protein complex characterization and proteome exploration," Nat Biotechnol, Oct. 1999, vol. 17, 1030-1032; doi:10.1038/13732.

Roach "Multisite and Hierarchal Protein Phosphorylation," J Biol Chem, 1991, vol. 266, No. 22, pp. 14139-14142; The American Society for Biochemistry and Molecular Biology, Inc.

Rush et al. "Immunoaffinity profiling of tyrosine phosphorylation in cancer cells," Nat Biotechnol, Jan. 2005, vol. 23, No. 1, pp. 94-101; doi:10.1038/nbt1046.

Ruvinsky et al. "Ribosomal protein S6 phosphorylation is a determinant of cell size and glucose homeostasis," Gene Develop, 2005, vol. 19, pp. 2199-2211; doi: 10.1101/gad.351605.

Saito et al. "Drug delivery strategy utilizing conjugation via reversible disulfide linkages: role and site of a cellular reducing activities," Adv Drug Del Rev, 2003, vol. 55, pp. 199-215; Elsevier.

Schreier et al. "Targeting of Liposomes to Cells Expressing CD4 Using Glycosylphosphatidylinositol-anchored gp120," J Biol Chem, Mar. 25, 1994, vol. 269, No. 12, pp. 9090-9098; The American Society for Biochemistry and Molecular Biology, Inc.

Schummer et al. "Inexpensive Handheld Device for the Construction of High-Density Nucleic Acid Arrays," BioTechniques, Dec. 1997, vol. 23, iss 6, pp. 1087-1092; Informa BioSciences, New York, New York.

Schwartz et al. "An iterative statistical approach to the identification of protein phosphorylation motifs from large-scale data sets," Nat Biotechnol, Nov. 2005, vol. 23, No. 11, pp. 1391-1398; doi:10.1038/nbt1146.

Senter et al. "Selective activation of anticancer prodrugs by monoclonal antobody—enzyme conjugates," Adv Drug Del Rev, 2001, vol. 53, pp. 247-264; Elsevier.

Shields et al. "High Resolution Mapping of the Binding Site on Human IgG1 for FcγRI, FcγRII, FcγRIII, and FcRn and Design of IgG1 Variants with Improved Binding to the FcγR," J Biol Chem, Mar. 2, 2001, vol. 276, No. 9, pp. 6591-6604; doi:10.1074/jbc.M009483200.

Shields et al. "Lack of Fucose on Human IgG1 N-Linked Oligosaccharide Improves Binding to Human FcγRIII and Antibody-dependent Cellular Toxicity," J Biol Chem, May 1, 2002, vol. 277, pp. 26733-26740; doi:10.1074/jbc.M202069200.

Solinas-Toldo et al. "Matrix-Based Comparative Genomic Hybridization: Biochips to Screen for Genomic Imbalances," Gen Chromosomes Cancer, 1997, vol. 20, pp. 399-407; Wiley-Liss, Inc.

Stiles et al. "Live-specific deletion of negative regulator Pten results in fatty liver and insulin hypersensitivity," Proc Natl Acad Sci, USA, Feb. 17, 2004, vol. 101, No. 7; doi:10.1073/pnas.0308617100.

Tao et al. "Quantitative phosphoproteome analysis using a dendrimer conjugation chemistry and tandem mass spectrometry," Nat Method, Aug. 2005, vol. 2, No. 8, pp. 591-598; doi:10.1038/nmeth776.

Thorpe et al. "The Preparation and Cytotoxic Properties of Antibody-Toxin Conjugates," Immunological Rev, Feb. 1982, vol. 62, iss 1, pp. 119-158; doi: 10.1111/j.1600-065X.1982.tb00392.x.

Tomlinson et al. "The repertoire of human germline V sequences reveals about fifty groups of V segments with different hypervariable loops," J Mol Biol, vol. 227, iss 3, Oct. 5, 1992, pp. 776-798; http://dx.doi.org/10.1016/0022-2836(92)90223-7.

Trail et al. "Monoclonal antibody drug immunoconjugates for targeted treatment of cancer," Cancer Immunol Immunother, vol. 52, No. 5, 328-337; doi: 10.1007/s00262-002-0352-9, (2003).

Umana et al. "Engineered glycoforms of an antineuroblastoma IgG1 with optimized antibody-dependent cellular cytotoxic activity," Nat Biotechnol, Feb. 1999, vol. 17, pp. 176-180; doi:10.1038/6179.

Umezawa et al. "Liposome Targeting to Mouse Brain: Mannose as a Recognition Marker," Biochem Biophys Res Commun, Jun. 30, 1988, vol. 153, No. 3, pp. 1038-1044; Academic Press, Inc.

(56) References Cited

OTHER PUBLICATIONS

Villen et al. "Large-scale phosphorylation analysis of a mouse liver," Proc Natl Acad Sci, USA, Jan. 30, 2007, vol. 104, No. 5, pp. 1488-1493; doi:10.1073/pnas.0609836104.

Ward et al. "Binding activities of a repertoire of single immunoglobulin variable domains secreted from *Escherichia coli*," Nature, Oct. 12, 1989, vol. 341, pp. 544-546; doi:10.1038/341544a0.

Yang "Multisite protein modification and intramolecular signaling," Oncogene, 2005, vol. 24, pp. 1653-1662; doi:10.1038/sj.onc.1208173.

Yen et al. "Molecular Cloning of a Lipolysis-stimulated Remnant Receptor Expressed in the Liver," J Biol Chem, May 7, 1999, vol. 274, No. 19, pp. 13390-13398; doi:10.1074/jbc.274.19.13390.

Zhang et al. "High Throughput Quantitative Analysis of Serum Proteins Using Glycopeptide Capture and Liquid Chromatography Mass Spectrometry," Mol Cell Proteomics, 2005, vol. 4, pp. 144-155; doi:10.1074/mcp.M400090-MCP200.

Zhou et al. "A systematic approach to the analysis of protein phosphorylation," Nat Biotechnol, Apr. 2001, vol. 19, pp. 375-378; doi:10.1038/86777.

\* cited by examiner

Figure 1
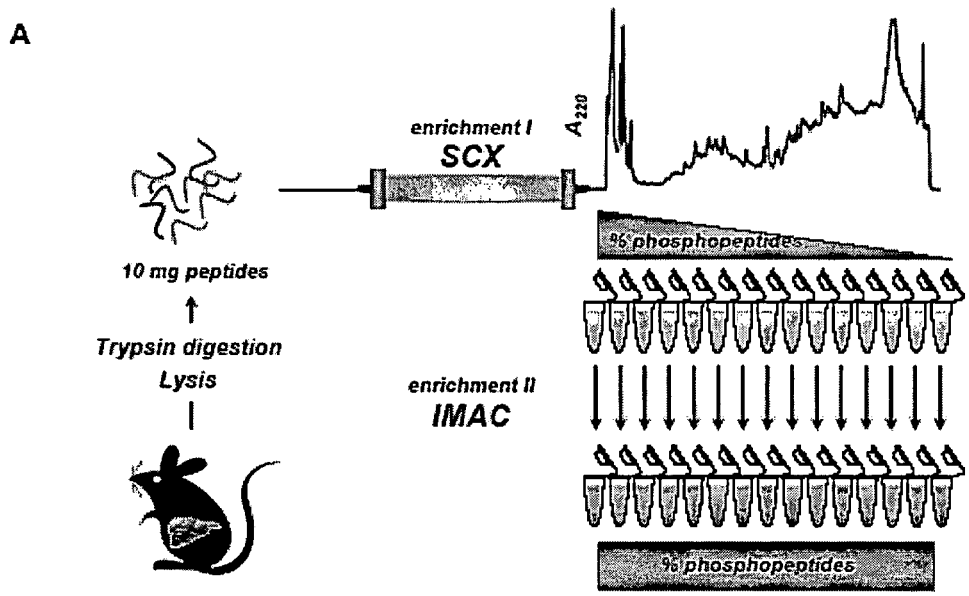
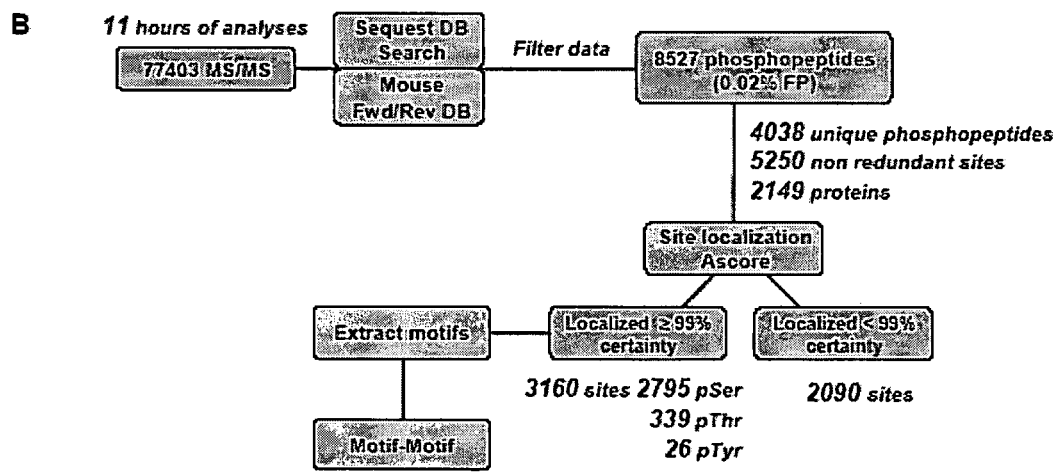

Figure 6
SINGLY PHOSPHORYLATED
DOUBLY PHOSPHORYLATED

Figure 9
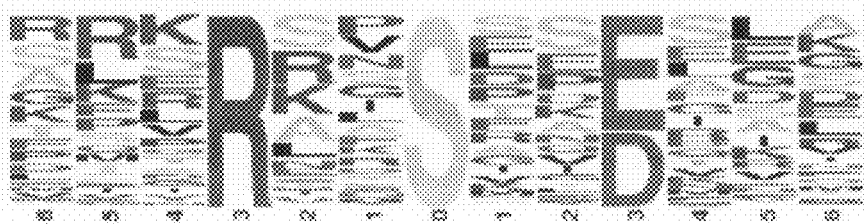
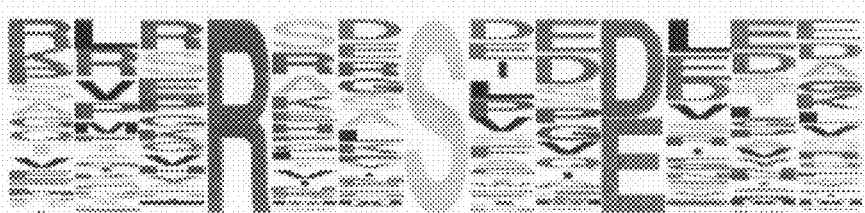

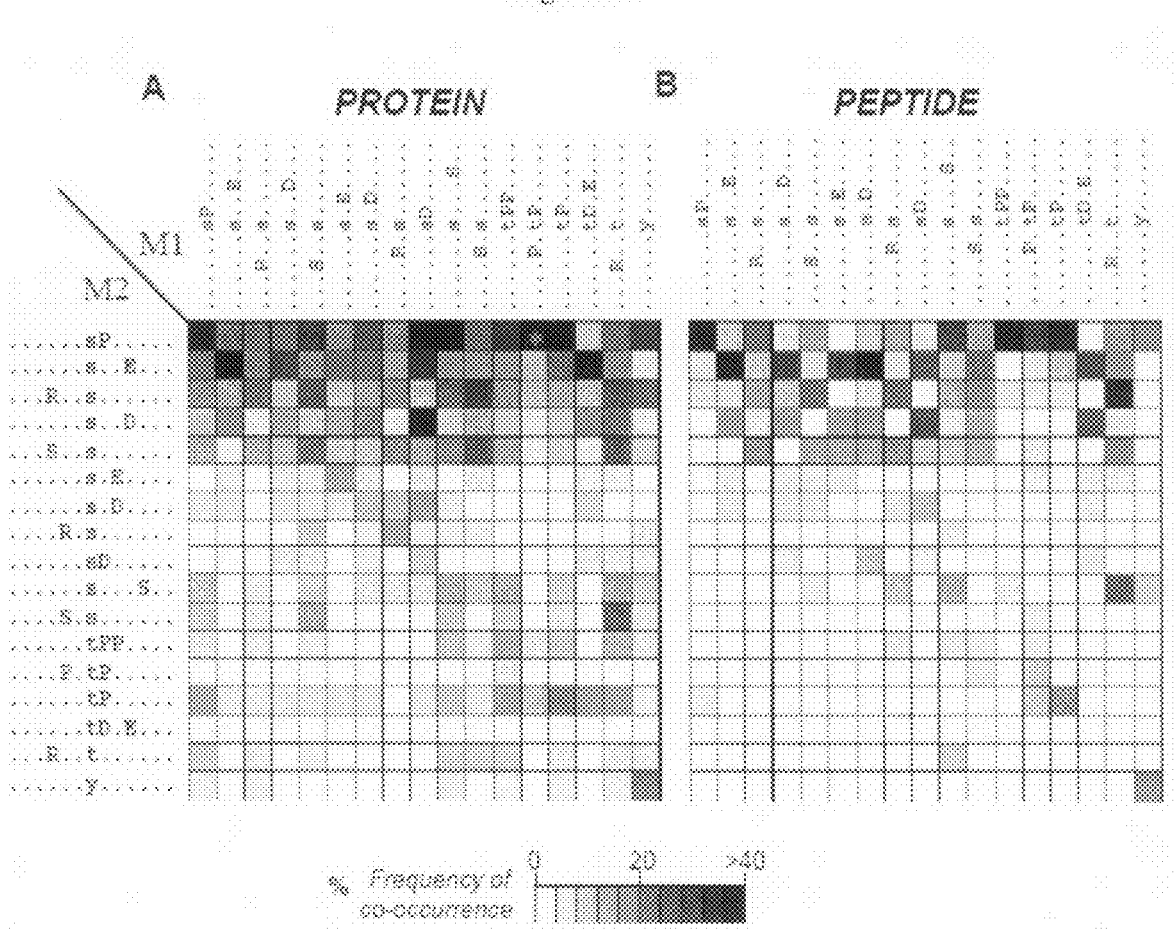

SEQUENCE LISTING

```
<160> NUMBER OF SEQ ID NOS: 52

<210> SEQ ID NO 1
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Xaa is any naturally occurring or synthetic
      amino acid and Ser is a phosphorylated serine

<400> SEQUENCE: 1

Arg Xaa Xaa Ser
1

<210> SEQ ID NO 2
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Xaa is any naturally occurring or synthetic
      amino acid and Ser is a phosphorylated serine

<400> SEQUENCE: 2

Ser Xaa Xaa Glu
1

<210> SEQ ID NO 3
<211> LENGTH: 2
<212> TYPE: PRT
<213> ORGANISM: Mus musculus
<220> FEATURE:
<221> NAME/KEY: MISC_FEATURE
<222> LOCATION: (1)..(2)
<223> OTHER INFORMATION: Ser is a phosphorylated serine

<400> SEQUENCE: 3

Ser Pro
1
```

-continued

```
<210> SEQ ID NO 4
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Xaa is any naturally occurring or synthetic
      amino acid and Ser is a phosphorylated serine

<400> SEQUENCE: 4

Arg Xaa Xaa Ser Pro
1               5

<210> SEQ ID NO 5
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Xaa is any naturally occurring or synthetic
      amino acid and Ser at position 5 in the sequence is a
      phosphorylated serine

<400> SEQUENCE: 5

Ser Pro Xaa Xaa Ser Pro
1               5

<210> SEQ ID NO 6
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Xaa is any naturally occurring or synthetic
      amino acid and Ser is a phosphorylated serine

<400> SEQUENCE: 6

Ser Pro Xaa Xaa Xaa Xaa Arg
1               5

<210> SEQ ID NO 7
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Xaa is any naturally occurring or synthetic
      amino acid and Ser at position 7 in the sequence is a
      phosphorylated serine

<400> SEQUENCE: 7

Arg Xaa Xaa Ser Xaa Xaa Ser
1               5

<210> SEQ ID NO 8
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Xaa is any naturally occurring or synthetic
      amino acid and Ser at position 1 in the sequence is a
      phosphorylated serine

<400> SEQUENCE: 8
```

```
Ser Xaa Xaa Ser
1

<210> SEQ ID NO 9
<211> LENGTH: 3
<212> TYPE: PRT
<213> ORGANISM: Mus musculus
<220> FEATURE:
<221> NAME/KEY: MISC_FEATURE
<222> LOCATION: (1)..(3)
<223> OTHER INFORMATION: Thr is a phosphorylated threonine

<400> SEQUENCE: 9

Thr Pro Pro
1

<210> SEQ ID NO 10
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Xaa is any naturally occurring or synthetic
      amino acid and Ser is a phosphorylated serine

<400> SEQUENCE: 10

Ser Pro Xaa Xaa Ser Pro
1               5

<210> SEQ ID NO 11
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Ser is a phosphorylated serine

<400> SEQUENCE: 11

Ser Pro Ser Pro
1

<210> SEQ ID NO 12
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Ser is a phosphorylated serine

<400> SEQUENCE: 12

Ser Asp Ser Glu
1

<210> SEQ ID NO 13
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Xaa is any naturally occurring or synthetic
      amino acid and Ser is a phosphorylated serine

<400> SEQUENCE: 13

Ser Ser Xaa Glu Glu
1               5
```

```
<210> SEQ ID NO 14
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Xaa is any naturally occurring or synthetic
      amino acid and Ser is a phosphorylated serine

<400> SEQUENCE: 14

Ser Pro Xaa Ser
1

<210> SEQ ID NO 15
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Xaa is any naturally occurring or synthetic
      amino acid and Ser is a phosphorylated serine

<400> SEQUENCE: 15

Ser Xaa Ser Glu Xaa Glu
1               5

<210> SEQ ID NO 16
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Xaa is any naturally occurring or synthetic
      amino acid and Ser is a phosphorylated serine

<400> SEQUENCE: 16

Ser Xaa Xaa Xaa Ser Pro
1               5

<210> SEQ ID NO 17
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Xaa is any naturally occurring or synthetic
      amino acid and Ser is a phosphorylated serine

<400> SEQUENCE: 17

Ser Ser Xaa Xaa Glu
1               5

<210> SEQ ID NO 18
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Xaa is any naturally occurring or synthetic
      amino acid and Ser is a phosphorylated serine

<400> SEQUENCE: 18

Arg Xaa Xaa Ser Xaa Xaa Ser
1               5
```

```
<210> SEQ ID NO 19
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Xaa is any naturally occurring or synthetic
      amino acid and Ser is a phosphorylated serine

<400> SEQUENCE: 19

Ser Xaa Xaa Ser Xaa Xaa Glu
1               5

<210> SEQ ID NO 20
<211> LENGTH: 4
<212> TYPE: PRT
<213> ORGANISM: Mus musculus
<220> FEATURE:
<221> NAME/KEY: MISC_FEATURE
<222> LOCATION: (1)..(4)
<223> OTHER INFORMATION: Xaa is any naturally occurring or synthetic
      amino acid and Ser is a phosphorylated serine

<400> SEQUENCE: 20

Ser Xaa Ser Glu
1

<210> SEQ ID NO 21
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Xaa is any naturally occurring or synthetic
      amino acid and Ser is a phosphorylated serine

<400> SEQUENCE: 21

Arg Xaa Xaa Ser Xaa Ser
1               5

<210> SEQ ID NO 22
<211> LENGTH: 6
<212> TYPE: PRT
<213> ORGANISM: Mus musculus
<220> FEATURE:
<221> NAME/KEY: MISC_FEATURE
<222> LOCATION: (1)..(6)
<223> OTHER INFORMATION: Xaa is any naturally occurring or synthetic
      amino acid and Ser is a phosphorylated serine

<400> SEQUENCE: 22

Ser Ser Xaa Xaa Xaa Asp
1               5

<210> SEQ ID NO 23
<211> LENGTH: 5
<212> TYPE: PRT
<213> ORGANISM: Mus musculus
<220> FEATURE:
<221> NAME/KEY: MISC_FEATURE
<222> LOCATION: (1)..(5)
<223> OTHER INFORMATION: Xaa is any naturally occurring or synthetic
      amino acid and Ser is a phosphorylated serine

<400> SEQUENCE: 23

Ser Xaa Xaa Ser Leu
1               5
```

```
<210> SEQ ID NO 24
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Xaa is any naturally occurring or synthetic
      amino acid and Ser is a phosphorylated serine

<400> SEQUENCE: 24

Arg Xaa Xaa Ser Xaa Xaa Asp
1               5

<210> SEQ ID NO 25
<211> LENGTH: 7
<212> TYPE: PRT
<213> ORGANISM: Mus musculus
<220> FEATURE:
<221> NAME/KEY: MISC_FEATURE
<222> LOCATION: (1)..(7)
<223> OTHER INFORMATION: Xaa is any naturally occurring or synthetic
      amino acid and Ser is a phosphorylated serine

<400> SEQUENCE: 25

Arg Xaa Xaa Ser Xaa Xaa Glu
1               5

<210> SEQ ID NO 26
<211> LENGTH: 15
<212> TYPE: PRT
<213> ORGANISM: Mus musculus
<220> FEATURE:
<221> NAME/KEY: MISC_FEATURE
<222> LOCATION: (1)..(15)
<223> OTHER INFORMATION: Ser at positions 3 and 8 in the sequence are
      phosphorylated serines

<400> SEQUENCE: 26

Thr Ser Ser Val Gly Gly His Ser Ser Gln Val Pro Leu Leu Arg
1               5                   10                  15

<210> SEQ ID NO 27
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: Ser at positions 3 and 7 in the sequence are
      phosphorylated serines

<400> SEQUENCE: 27

Ala Met Ser Glu Val Thr Ser Leu His Glu Asp Asp Trp Arg
1               5                   10

<210> SEQ ID NO 28
<211> LENGTH: 18
<212> TYPE: PRT
<213> ORGANISM: Mus musculus
<220> FEATURE:
<221> NAME/KEY: MISC_FEATURE
<222> LOCATION: (1)..(18)
<223> OTHER INFORMATION: Ser at position 16 in the sequence is a
      phosphorylated serine

<400> SEQUENCE: 28

Ala Pro Ala Leu Thr Pro Ile Arg Asp Glu Glu Trp Asn Arg His Ser
1               5                   10                  15
```

Pro Arg

```
<210> SEQ ID NO 29
<211> LENGTH: 26
<212> TYPE: PRT
<213> ORGANISM: Mus musculus
<220> FEATURE:
<221> NAME/KEY: MISC_FEATURE
<222> LOCATION: (1)..(26)
<223> OTHER INFORMATION: Ser at positions 1, 13, 16, and 24 in the
      sequence are phosphorylated serines

<400> SEQUENCE: 29

Ser Val Asp Ala Leu Asp Asp Ile Asn Arg Pro Gly Ser Thr Glu Ser
1               5                   10                  15

Gly Arg Ser Ser Pro Pro Ser Ser Gly Arg
            20                  25

<210> SEQ ID NO 30
<211> LENGTH: 14
<212> TYPE: PRT
<213> ORGANISM: Mus musculus
<220> FEATURE:
<221> NAME/KEY: MISC_FEATURE
<222> LOCATION: (1)..(14)
<223> OTHER INFORMATION: Ser at position 3 in the sequence is a
      phosphorylated serine

<400> SEQUENCE: 30

Ser Arg Ser Arg Asp Asp Leu Tyr Asp Pro Asp Asp Pro Arg
1               5                   10

<210> SEQ ID NO 31
<211> LENGTH: 11
<212> TYPE: PRT
<213> ORGANISM: Mus musculus
<220> FEATURE:
<221> NAME/KEY: MISC_FEATURE
<222> LOCATION: (1)..(11)
<223> OTHER INFORMATION: Ser at positions 5 and 8 in the sequence are
      phosphorylated serines

<400> SEQUENCE: 31

Asn Leu Ala Leu Ser Arg Glu Ser Leu Val Val
1               5                   10

<210> SEQ ID NO 32
<211> LENGTH: 4
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 32

Pro Xaa Ser Pro
1

<210> SEQ ID NO 33
<211> LENGTH: 6
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
```

```
<222> LOCATION: (5)..(5)
<223> OTHER INFORMATION: Xaa can be any naturally occurring amino acid

<400> SEQUENCE: 33

Ser Asp Xaa Glu Xaa Glu
1               5

<210> SEQ ID NO 34
<211> LENGTH: 3
<212> TYPE: PRT
<213> ORGANISM: Mus musculus

<400> SEQUENCE: 34

Ser Pro Arg
1

<210> SEQ ID NO 35
<211> LENGTH: 4
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 35

Arg Arg Xaa Ser
1

<210> SEQ ID NO 36
<211> LENGTH: 5
<212> TYPE: PRT
<213> ORGANISM: Mus musculus
<220> FEATURE:
<221> NAME/KEY: misc_feature
<222> LOCATION: (2)..(3)
<223> OTHER INFORMATION: Xaa can be any naturally occurring amino acid

<400> SEQUENCE: 36

Ser Xaa Xaa Glu Glu
1               5

<210> SEQ ID NO 37
<211> LENGTH: 6
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 37

Leu Xaa Arg Xaa Xaa Ser
1               5

<210> SEQ ID NO 38
<211> LENGTH: 4
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 38
```

Ser Asp Xaa Glu
1

<210> SEQ ID NO 39
<211> LENGTH: 4
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 39

Ser Asp Xaa Asp
1

<210> SEQ ID NO 40
<211> LENGTH: 6
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 40

Arg Xaa Arg Xaa Xaa Ser
1               5

<210> SEQ ID NO 41
<211> LENGTH: 3
<212> TYPE: PRT
<213> ORGANISM: Mus musculus

<400> SEQUENCE: 41

Ser Glu Glu
1

<210> SEQ ID NO 42
<211> LENGTH: 3
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 42

Ser Xaa Asp
1

<210> SEQ ID NO 43
<211> LENGTH: 3
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 43

Ser Xaa Glu
1

<210> SEQ ID NO 44

```
<211> LENGTH: 2
<212> TYPE: PRT
<213> ORGANISM: Mus musculus

<400> SEQUENCE: 44

Asp Ser
1

<210> SEQ ID NO 45
<211> LENGTH: 4
<212> TYPE: PRT
<213> ORGANISM: Mus musculus
<220> FEATURE:
<221> NAME/KEY: misc_feature
<222> LOCATION: (2)..(3)
<223> OTHER INFORMATION: Xaa can be any naturally occurring amino acid

<400> SEQUENCE: 45

Ser Xaa Xaa Asp
1

<210> SEQ ID NO 46
<211> LENGTH: 3
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 46

Arg Xaa Ser
1

<210> SEQ ID NO 47
<211> LENGTH: 4
<212> TYPE: PRT
<213> ORGANISM: Mus musculus
<220> FEATURE:
<221> NAME/KEY: misc_feature
<222> LOCATION: (2)..(2)
<223> OTHER INFORMATION: Xaa can be any naturally occurring amino acid

<400> SEQUENCE: 47

Pro Xaa Thr Pro
1

<210> SEQ ID NO 48
<211> LENGTH: 2
<212> TYPE: PRT
<213> ORGANISM: Mus musculus

<400> SEQUENCE: 48

Thr Pro
1

<210> SEQ ID NO 49
<211> LENGTH: 4
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid

<400> SEQUENCE: 49

Thr Asp Xaa Glu
1
```

```
<210> SEQ ID NO 50
<211> LENGTH: 4
<212> TYPE: PRT
<213> ORGANISM: Mus musculus
<220> FEATURE:
<221> NAME/KEY: misc_feature
<222> LOCATION: (2)..(3)
<223> OTHER INFORMATION: Xaa can be any naturally occurring amino acid

<400> SEQUENCE: 50

Arg Xaa Xaa Thr
1

<210> SEQ ID NO 51
<211> LENGTH: 5
<212> TYPE: PRT
<213> ORGANISM: Mus musculus
<220> FEATURE:
<221> NAME/KEY: misc_feature
<222> LOCATION: (3)..(4)
<223> OTHER INFORMATION: Xaa can be any naturally occurring amino acid

<400> SEQUENCE: 51

Ser Ser Xaa Xaa Glu
1               5

<210> SEQ ID NO 52
<211> LENGTH: 5
<212> TYPE: PRT
<213> ORGANISM: Mus musculus
<220> FEATURE:
<221> NAME/KEY: misc_feature
<222> LOCATION: (2)..(4)
<223> OTHER INFORMATION: Xaa can be any naturally occurring amino acid

<400> SEQUENCE: 52

Ser Xaa Xaa Xaa Ser
1               5
```

PHOSPHOPEPTIDE COMPOSITIONS AND ANTI-PHOSPHOPEPTIDE ANTIBODY COMPOSITIONS AND METHODS OF DETECTING PHOSPHORYLATED PEPTIDES

RELATED APPLICATION

The present application claims the benefit of provisional application Ser. No. 60/855,664 filed in the U.S. Patent and Trademark Office on Oct. 31, 2006.

GOVERNMENT SUPPORT

The invention was supported in part by funding from the National Institutes of Health grants GM67945 and HG3456. The government has certain rights in the invention.

TECHNICAL FIELD

The present invention relates to phosphopeptide compositions and anti-phosphopeptide antibody compositions and methods of detecting phosphorylated peptides.

BACKGROUND

Protein phosphorylation is an important regulatory event in eukaryotic cells, guiding primary biological processes such as cell division, growth, migration, differentiation and intercellular communication (Hunter, 2000; Pawson and Scott, 2005). Protein phosphorylation plays an important role in normal organ development and function, such as liver, kidney, and other organismal tissue systems.

Several phosphorylation-related (PI3K and Akt signaling) liver phenotypes have been reported that are related to altered lipid and glucose metabolism through insulin control (Du et al., 2003; Stiles et al., 2004) and liver regeneration (ribosomal protein S6; Ruvinsky et al., 2005). Previously, only two studies have examined phosphorylation sites from primary liver tissue with observation of 26 sites (Jin et al., 2004) and 339 sites (Moser and White, 2006).

Proteins often contain multiple sites of phosphorylation, resulting in a high degree of versatility in functional regulation. Those sites can be modified independently or in a concerted manner to modulate a range of protein functions, from a single specific activity to higher order processes (Cohen, 2000; Roach, 1991; Yang, 2005). Each additional phosphorylation site attributed to a protein represents an exponential increase in the total number of possible molecular states and, therefore, in complexity and fine tuning potential for regulation.

Although the phosphoproteome of mammalian cells in culture has been extensively studied, acquired knowledge is limited to less than 8,000 known phosphorylation sites (Diella et al., 2004; Hornbeck et al., 2004).

A problem in conducting large-scale phosphorylation analysis concerns data processing and validation. There are three main issues. First, studies of posttranslational modifications cannot rely on redundant peptide identifications for correctness, i.e., multiple unique peptides assigned to the same protein. This results in the net confidence of identification resting solely on single peptide identifications.

Second, during protein fragmentation for amino acid sequence identification, phosphoserine- and phosphothreonine-containing peptides can produce fragmentation patterns that are often dominated by β-elimination products through loss of neutral phosphoric acid, which results in suppression of sequence-informative ions and consequently produces lower scores than unmodified peptides during database spectral matching.

Third, the presence of multiple serine, threonine and tyrosine candidate residues in a phosphopeptide can produce ambiguity when assigning the precise site of phosphorylation.

The prior art has previously resorted to tedious manual validation after database searching, which can be subjective and has become impractical as data sets have grown in size. There is a clear risk in supplying a phosphorylation site without also establishing an associated probability of correct site localization, in particular when attempting to associate a function for that particular modification.

There is a need for compositions and methods to obtain phosphorylated peptides and antibodies of these phosphorylated peptides.

SUMMARY

An aspect of the invention provides an amino acid sequence phosphorylation site motif having a consensus sequence selected from the group consisting of: Rxxs (SEQ ID NO: 1); sxxE (SEQ ID NO: 2); sP (SEQ ID NO: 3); RxxsP (SEQ ID NO: 4); SPxxsP (SEQ ID NO: 5); sPxxxxR (SEQ ID NO: 6); RxxSxxs (SEQ ID NO: 7); sxxS (SEQ ID NO: 8); tPP (SEQ ID NO: 9); sPxxsP (SEQ ID NO: 10); sPsP (SEQ ID NO: 11); sDsE (SEQ ID NO: 12); ssxEE (SEQ ID NO: 13); sPxs (SEQ ID NO: 14); sxsExE (SEQ ID NO: 15); sxxxsP (SEQ ID NO: 16); ssxxE (SEQ ID NO: 17); Rxxsxxs (SEQ ID NO: 18); sxxsxxE (SEQ ID NO: 19); sxsE (SEQ ID NO: 20); Rxxsxs (SEQ ID NO: 21); ssxxxD (SEQ ID NO: 22); and sxxsL (SEQ ID NO: 23); RxxsxxD (SEQ ID NO: 24); and RxxsxxE (SEQ ID NO: 25); in which "x" is any naturally occurring or synthetic amino acid; "s" is a phosphorylated serine; "t" is a phosphorylated threonine; and an upper case letter indicates the single letter amino acid code.

In a related embodiment, the amino acid sequence phosphorylation site motifs of SEQ ID NOs: 1-9 are amino acid sequences with at least a single phosphorylation site motif. In another related embodiment, the amino acid sequence phosphorylation site motifs of SEQ ID NOs: 10-23 are amino acid sequences with at least a double phosphorylation site motif. In yet another related embodiment, the amino acid sequence phosphorylation site motifs of SEQ ID NOs: 24-25 are amino acid sequences with a dipolar phosphorylation site motif.

In certain embodiments, the invention provides an amino acid phosphorylation site within a peptide, the peptide having a sequence selected from the group consisting of: TSS#VGGHS#SQVPLLR (SEQ ID NO: 26); AMS#EVTS#LHEDDWR (SEQ ID NO: 27); APALTPIRDEEWNRHS#PR (SEQ ID NO: 28); S#VDALDDINRPGS#TES#GRSSPPSS#GR (SEQ ID NO: 29); SRS#RDDLYDPDDPR (SEQ ID NO: 30) and NLALS#RES#LVV (SEQ ID NO: 31); in which "#" is the position of the phosphorylation site within the peptide. In a related embodiment, the amino acid sequence of SEQ ID NOs: 26-31 are in a lipolysis-stimulated receptor. In another related embodiment, phosphorylation is modulated by lipolysis. In a further related embodiment, lipolysis is an in vivo process.

In other embodiments, the invention provides a method of identifying phosphorylation sites within a plurality of proteins or peptides or mixture thereof. The method includes, subjecting the protein or peptide to phosphate enrichment and analyzing the phosphate enriched protein or peptide using microcapillary liquid chromatography coupled online to a tandem mass spectrometer (LC-MS/MS) to produce a raw data set of spectra and applying at least one filtering criterion to the raw data set of spectra to obtain a refined data set of spectra; and comparing the refined data set of spectra to a protein database in a forward direction to identify at least one phosphorylated amino acid residue in each of the phosphorylation sites within the sequences.

In a related embodiment, an additional step of the above method includes applying a probability-based algorithm to the refined data set of spectra to associate phosphorylation sites to a position within the protein or peptide. In yet another related embodiment of the above method, another additional step includes comparing the refined data set of spectra to the protein database in a reverse direction to calculate a false positive rate such that the false positive rate is used to remove redundant spectra of amino acid sequences from the refined data set. In yet another related embodiment of the above method, another additional step includes applying an algorithm that compares the intrinsic alignment of phospho-residues to a dynamic statistical background to extract phosphorylation motifs from phosphorylation sites.

In still another related embodiment of the above method, the filtering criterion is at least one selected from the group consisting of: mass accuracy; tryptic state; solution charge state; and SEQUEST scoring. In still another related embodiment of the above method, the phosphate enrichment further includes at least one procedure selected from the group consisting of: β-elimination; phosphoramidate chemistry; peptide immunoprecipitation with phospho-specific motif antibodies; affinity purification through metal complexation with a phosphate group; and solution charge-based enrichment by strong cation exchange chromatography.

In certain embodiments of the above method, prior to subjecting the plurality of proteins or peptides or mixture of these to phosphate enrichment, the proteins or peptides or mixture of these are digested with trypsin.

In another related embodiment of the above method, the proteins or peptides or mixture of these is at least one obtained from: a tissue; an organ; an organism; a biopsy sample; and a biological fluid. In certain embodiments, the proteins or peptides are substantially pure. In other embodiments, the protein or peptide is mammalian. In further embodiments, the protein or peptide is human.

In certain embodiments, the invention provides a plurality of amino acid sequences, each amino acid sequence having at least one phosphorylation site such that the plurality is obtained from a plurality of proteins or peptides or mixtures of these. The phosphorylation site identified by a process including, subjecting the protein or peptide to phosphate enrichment and analyzing the phosphate enriched protein or peptide using microcapillary liquid chromatography coupled online to a tandem mass spectrometer (LC-MS/MS) to produce a raw data set of spectra and applying at least one filtering criterion to the raw data set of spectra to obtain a refined data set of spectra; comparing the refined data set of spectra to a protein database in a forward direction to identify at least one phosphorylated amino acid residue in each of the phosphorylation sites within the sequences and comparing the refined data set of spectra to the protein database in a reverse direction to calculate a false positive rate such that the false positive rate is used to remove redundant spectra of amino acid sequences from the refined data set; and applying a first probability-based algorithm to the data set of spectra to associate the phosphorylation sites to a position within each of the plurality of proteins or peptides or mixtures of these.

In a related embodiment of the process, an additional step includes applying a second algorithm that compares the intrinsic alignment of phospho-residues to a dynamic statistical background to obtain at least one phosphorylation motif from the amino acid sequences of the phosphorylation sites.

In another related embodiment of the process, the filtering criterion is at least one selected from the group consisting of: mass accuracy; tryptic state; solution charge state; and SEQUEST scoring. In yet another related embodiment of the above process, the phosphate enrichment further comprises at least one procedure selected from the group consisting of: β-elimination; phosphoramidate chemistry; peptide immunoprecipitation with phospho-specific motif antibodies; affinity purification through metal complexation with a phosphate group; and solution charge-based enrichment by strong cation exchange chromatography.

In certain embodiments of the above process, prior to subjecting the plurality of proteins or peptides or mixture of these to phosphate enrichment, the proteins or peptides or mixture of these are digested with trypsin.

In another related embodiment of the above process, the proteins or peptides or mixture of these is selected from at least one obtained from: a tissue; an organ; an organism; a biopsy sample; and a biological fluid. In certain related embodiments of the process, the proteins or peptides are substantially pure. Alternatively, the proteins or peptides are in a crude extract. In other related embodiments of the process, the proteins or peptides are mammalian. In still other related embodiments of the process, the proteins or peptides are human.

In certain embodiments, the invention provides an amino acid phosphorylation site within a peptide, the peptide having a sequence selected from the group consisting of those sequences shown in claim 29, such that "#" is the position of the phosphorylation site within the peptide and "*" is an oxidized methionine.

Another aspect of the invention provides an isolated antibody or functional fragment of the antibody comprising an antigen-binding region that is specific for an amino acid phosphorylation site within a target protein or peptide or mixture of these according to any of the above sequences, in which the antibody or functional fragment of the antibody binds the phosphorylation site within the protein or peptide.

In a related embodiment of the isolated antibody or functional fragment of the antibody, the protein or peptide is phosphorylated. In another related embodiment of the isolated antibody or functional fragment of the antibody, the protein or peptide is not phosphorylated. In still another related embodiment, the isolated antibody or functional fragment of the antibody is an isolated antigen-binding region Fv fragment.

In other related embodiments, the isolated antibody is an IgG. In still other related embodiments, the isolated antibody is an IgG1 or an IgG4. In certain embodiments, the isolated antibody or functional fragment is a Fab or scFv antibody fragment.

In another embodiment, the invention provides an immunoconjugate having a first component which is the above antibody or fragment of the antibody. In a related embodiment, the immunoconjugate has a second component. In still another related embodiment, the immunoconjugate further includes a cytotoxin.

In yet another related embodiment, the second component of the above immunoconjugate is a binding protein or antibody having a binding specificity for a target that is different from the phosphorylated protein or peptide. In certain embodiments, the invention provides a bispecific antibody.

Another aspect of the present invention is an array for detecting a binding agent that binds to a phosphorylation site within a phosphorylated peptide, the array having a plurality of phosphorylated peptides according to any of the above sequences, such that each phosphorylated peptide is immobilized to a discrete and known spot on a substrate surface to form an array of phosphorylated peptides.

In a related embodiment of the array, the phosphorylated peptides are spotted in duplicate or triplicate on the array. In still another related embodiment, a duplicate spot or triplicate spot has a different amount of immobilized phosphorylated peptide.

In certain embodiments, the array-immobilized phosphorylated peptides are covalently bound to the substrate surface. In other embodiments of the array, the phosphorylated peptides are at least about 2, 10, 20, 30, 50, or at least about 100 amino acid residues in length. In a related embodiment of the array, the phosphorylated peptides are at less than about 500, 250, 125, or 75 amino acid residues in length.

In another embodiment, the above array further includes at least one spot having phosphorylated peptide to act as a positive control. In another embodiment, the above array further includes at least one spot having a non-phosphorylated peptide to act as a negative control.

In certain embodiments of the array, the plurality of peptides further includes at least one non-phosphorylated peptide. In other embodiments of the array, the binding agent to be detected is a biological sample. In a related embodiment, the biological sample is at least one selected from the group consisting of: human; embryo; biopsy sample; blood sample; urine sample; cerebral spinal fluid sample; amniotic fluid sample; chorionic villus sample; and embryonic cell or embryo tissue sample.

In another embodiment, the invention provides an array for detecting a binding agent that binds to at least one of a plurality of the above antibodies specific for a phosphorylation site, such that each of plurality of the above antibodies is immobilized to a discrete and known spot on a substrate surface to form an array of antibodies.

Another aspect of the present invention is a method for detecting a binding agent, the method including providing an array having a plurality of any of the above phosphorylated peptides, each of the plurality immobilized to a discrete and known spot on a substrate surface to form an array of phosphorylated peptides; contacting the array with sample, such that a component of the sample forms at least one complex with at least one spot; and detecting the at least one complex bound to the phosphorylated peptide in a biological sample.

In a related embodiment of the method, the biological sample includes a detectable label. In another related embodiment, the label is detectable by a means selected from at least one of fluorescent, colorimetric, radioactive, and bioluminescent.

In yet another related embodiment of the method, an additional step includes use of a computer processor to analyze multicolor fluorescence imaging data.

Another aspect of the present invention provides a method for detecting a binding agent, the method including: providing an array comprising a plurality of the above antibodies, each of the plurality immobilized to a discrete and known spot on a substrate surface to form an array of antibodies; contacting the array with sample, so that a component of the sample forms at least one complex with at least one spot; and detecting the at least one complex bound to the antibodies in a biological sample.

In a related embodiment of the method, the biological sample comprises a detectable label. In another related embodiment, the label is detectable by a means selected from at least one of fluorescent, calorimetric, radioactive, and bioluminescent.

In yet another related embodiment, the method further includes use of a computer processor to analyze multicolor fluorescence imaging data.

In another aspect, the invention provides at least one isolated antibody or functional fragment thereof, in which the antibody is a plurality of antibodies wherein each of the plurality is immobilized to a discrete and known spot on a substrate surface to form an array of antibodies, wherein at least one of the antibodies of the plurality binds to a phosphorylation site within a protein or peptide.

In yet another aspect, the invention provides, a plurality of amino acid sequences, in which identifying the phosphorylation site further includes: providing each of the plurality of amino acid sequences in a phosphorylated form, and each of the phosphorylated amino acid sequences is immobilized to a discrete and known spot on a substrate surface to form an array of phosphorylated amino acid sequences; contacting the array with a biological sample wherein the sample contains a known control, under conditions such that at least one complex is formed; and detecting the at least one complex bound to the phosphorylated site within the amino acid sequence in the biological sample or in the control.

In a related embodiment of the plurality of amino acid sequences, the biological sample further includes a detectable label, in which the label is detectable by a means selected from at least one of fluorescent, calorimetric, radioactive, and bioluminescent.

In another aspect, the invention provides at least one isolated antibody or functional fragment thereof, in which identifying the phosphorylation site further comprises: providing each antibody immobilized to a discrete and known spot on a substrate surface to form an array of antibodies; contacting the array with a biological sample wherein the sample contains a known control, under conditions such that at least one complex is formed; and detecting the at least one complex bound to the antibodies in the biological sample or in the control.

In a related embodiment of the isolated antibody or functional fragment thereof, the biological sample further includes a detectable label, wherein the label is detectable by a means selected from at least one of fluorescent, calorimetric, radioactive, and bioluminescent.

BRIEF DESCRIPTION OF THE DRAWINGS

FIG. 1 is a drawing of a strategy used for the large-scale identification and characterization of phosphorylation sites from mouse liver. FIG. 1 panel A is a drawing of the strategy for sample preparation of the phosphopeptides and FIG. 1 panel B is a drawing of the strategy for data processing and analysis.

FIG. 2 panel A shows the number of phosphopeptides identified per fraction on the ordinate. FIG. 2 panel B shows percentage of phosphopeptides in each fraction containing one, two or three phosphorylation sites. FIG. 2 panel C shows percentage of phosphopeptides in each fraction with calculated solution charge states between −1 and +6. SCX chromatography separates primarily based on net solution charge state, and each phosphate group subtracts one net charge from a peptide.

FIG. 3 panel A shows an example of a phosphopeptide from lipolysis stimulated receptor (LSR) protein (SEQ ID NO: 26) in which only one of five possible residues (serine or threonine) can contain the phosphate. FIG. 3 panel B shows a tandem mass (MS/MS) spectrum for this phosphopeptide (SEQ ID NO: 26) showing fragmentation mostly at amide 28 bonds (b- and y-type fragment ions). FIG. 3 panel C shows site-determining ions predicted and identified for the serine marked with an asterisk. FIG. 3 panel D shows Ascore value distribution (and probability values) for all 5,250 sites.

FIG. 4 panel A is a graph showing the frequency of site detection with respect to protein sequence position. Protein sequences were divided into 1% bins and plotted by frequency. The green line shows the median value. A strong trend for C terminal (98-100% of the protein length) phosphorylation was observed.

FIG. 4 panel B is a graph showing the distribution of sites from the Phospho.ELM database, a curated resource containing sites from the literature. FIG. 4 panel C is a set of pie graphs, each showing classification of phosphorylation sites into the three most-general motif classes based on their position within the protein. All sites were classified into one of three general kinase motifs or as "Other" and their distributions at protein ends were determined: N-terminal is within first 10 amino acids; C-terminal is within last 10 amino acids; and Central is within all remaining residues. C-terminal sites had different distributions than N-terminal or Central sites.

FIG. 6 is a set of logo-like representations showing phosphorylation-specific motifs using the Motif-X algorithm.

FIG. 6 panels A-D show sequence logos for examples of single-phosphorylation motifs in which the phosphorylated residue (S or T) is centered: FIG. 6 panel A refers to proline-directed motifs; FIG. 6 panel B refers to basic motifs representative of CaM kinase and Akt kinase substrates, respectively; FIG. 6 panel C refers to acidic motif; and FIG. 6 panel D refers to proline-directed motif centered on threonine with strong preference for additional proline residues at C-terminal to the phosphate.

FIG. 6 panels E-H show examples of double-phosphorylation motifs in which secondary phosphorylated sites away from the central residue position are also phosphorylated: FIG. 6 panel E refers to proline-directed with additional phosphoserine at +4; FIG. 6 panel F refers to basic upstream and acidic downstream; FIG. 6 panel G refers to acidic motifs with two phosphoserines; and FIG. 6 panel H refers to phosphothreonine-directed motif.

FIG. 7 panel A, the left panel, shows co-occurrence frequencies at the protein level, in which the two phosphorylation events can be anywhere within the sequence. FIG. 7 panel B, right panel, shows co-occurrence frequencies at the peptide level, in which the two phosphorylation sites were identified within a single peptide.

For example, for specific motif M1=RxxsP, 126 occurrences were found. For M2=Acidic, 38 occurrences were found such that the likelihood of detecting a second phosphorylation event within an acidic motif given the known detection of RxxsP from a single protein was 38/126 or 30%.

Figure 8:
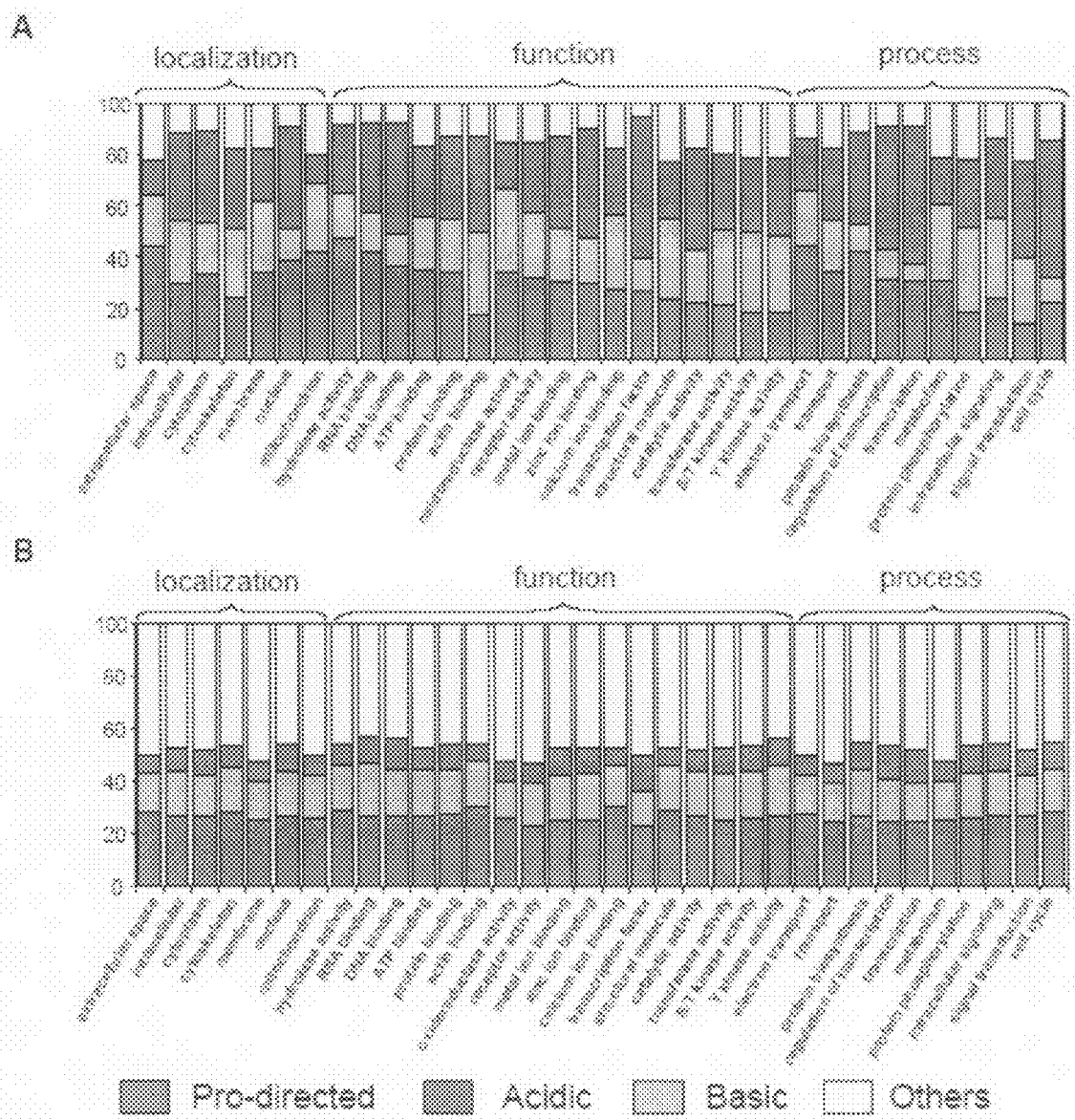

FIG. 8 is a set of graphs showing classification of phosphorylation sites into different phosphorylation sequence categories based on kinase substrate sequence preferences: acidic, basic, proline-directed, and others. FIG. 8 panel A is a graph showing diverse phosphorylation patterns for proteins belonging to different gene ontology annotation categories, regarding cellular localization, function or process. FIG. 8 panel B is a graph showing non-phosphorylated controls using every serine and threonine from each protein, showing minimal differences for sequence categories patterns depending upon gene ontology annotation.

FIG. 9 is a set of logo-like representations of phosphorylation motifs for sequences containing a dipolar motif Rxxsxx [E/D]. FIG. 9 panel A shows 109 sites from Phospho.ELM database matching the motif. FIG. 9 panel B shows 125 localized sites from the data set generated from implementation of the method of the present invention. The two extracted motifs were highly similar although higher frequencies for acidic residues on the C-terminal and basic residues on the N-terminal halves were observed in the data set generated from a method of the present invention, as compared to the Phospho.ELM entries.

FIG. 10 is a set of charts showing binary motif correlation in multiply-phosphorylated proteins, i.e., the frequency of detecting motif M1 in the presence of M2 within the same protein. Frequencies are then normalized to the total number of occurrences of M1. FIG. 10 panel A is a chart showing motifs analyzed for co-occurrence with other motifs. Phosphorylated residues within motifs are designated "s" and "t" for phosphoserine and phosphothreonine, respectively, and "." signifies any amino acid residue. For example, in FIG. 10 panel A, for M2=PxtP 36 occurrences were detected, from which 18 were found in the presence of M1=sP. The likelihood of detecting an sP was then calculated given the known detection of PxtP within a single protein as 18/36 or 50% (shown by a green asterisk). Applying the same analysis technique, FIG. 10 panel B is a chart showing binary motif correlation in multiply-phosphorylated peptides. In this way, both phosphorylation events were measured simultaneously and thus known to co-exist within the same protein molecule.

DETAILED DESCRIPTION

Protein phosphorylation plays an important role in normal development and function of organs, of which exemplary models are liver, kidney, brain, and pancreas. Several phosphorylation-related (PI3K and Akt signaling) liver phenotypes have been reported related to altered lipid and glucose metabolism via insulin control (Du et al., 2003; Stiles et al., 2004) and liver regeneration (ribosomal protein S6) (Ruvinsky et al., 2005).

As used herein, the term "phosphorylation site" or "phospho site" refers to an amino acid or amino acid sequence of a natural binding domain or a binding partner which is recognized by a kinase or phosphatase for the purpose of phosphorylation or dephosphorylation of the polypeptide or a portion thereof. A "site" additionally refers to the single amino acid which is phosphorylated or dephosphorylated. Generally, a phosphorylation site comprises as few as one but typically from about 1 to 10 or about 1 to 50 amino acids, i.e., less than the total number of amino acids present in the polypeptide.

The present invention in one embodiment provides methods combining tandem phosphopeptide enrichment methods, high performance mass spectrometry, and optimized database search/data filtering strategies as a powerful tool for surveying the phosphoproteome. Using the integrated analytical method of the present invention, 5,635 non-redundant phosphorylation sites from 2,328 proteins from mouse liver were identified (Villen et al., PNAS 104(5):1488-1493, 2007). From this list of sites, motifs for specific Ser/Thr kinases were extracted, including a "dipolar" motif.

In another embodiment, using the integrated analytical method of the present invention, phosphorylation sites from proteins from mouse kidney, brain, and pancreas were also identified. From this list of sites, motifs for specific Ser/Thr kinases were extracted.

A bioinformatic analysis of intra-protein phosphorylation motif coexistence was then performed. This analysis provides insights into global patterns of protein multisite phosphorylation.

Support for various embodiments of this invention is described in Villen et al., PNAS 104(5):1488-1493, 2007, which is incorporated by reference in its entirety herein.

Further support for the probability-based algorithm applied to the refined data set of spectra to associate phosphorylation sites to a position within the protein or peptide is described in a paper published online Sep. 10, 2006 in Nature Biotechnology by Beausoleil, S. A.; Judit, V.; Gerber, S. A.; Rush, J.; and Gygi S. P. entitled, "A probability-based approach for high-throughput protein phosphorylation analysis and site localization". This paper is incorporated by reference herein.

Further support for the algorithm that compares the intrinsic alignment of phospho-residues to a dynamic statistical background to extract phosphorylation motifs from phosphorylation sites is described in a paper published in Nature Biotechnology, 2005 vol. 23, 11:1391-11398 by Schwartz D.; and Gygi S. P. entitled, "An iterative statistical approach to the identification of protein phosphorylation motifs from large-scale data sets". This paper is incorporated by reference herein.

Antibodies

The present invention also relates to isolated antibodies that bind specifically to the phosphorylated peptides. The invention also provides isolated antibodies, methods of making such antibodies, immunoconjugates and bispecific molecules comprising such antibodies and pharmaceutical compositions containing the antibodies, immunoconjugates or bispecific molecules of the invention.

In order that the present invention may be more readily understood, certain terms are first defined. Additional definitions are set forth throughout the detailed description.

The term "immune response" refers to the action of, for example, lymphocytes, antigen presenting cells, phagocytic cells, granulocytes, and soluble macromolecules produced by the above cells or the liver (including antibodies, cytokines, and complement) that results in selective damage to, destruction of, or elimination from the human body of invading pathogens, cells or tissues infected with pathogens, cancerous cells, or, in cases of autoimmunity or pathological inflammation, normal human cells or tissues.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and capable of the transmission of such a signal across the plasma membrane of a cell. An example of a "cell surface receptor" of the present invention is the phosphorylated peptide to which other proteins bind.

The term "antibody" as referred to herein includes whole antibodies and any antigen binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, CH1, CH2 and CH3. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding portion" of an antibody (or simply "antigen portion"), as used herein, refers to full length or one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include a Fab fragment, a monovalent fragment consisting of the $V_L$, $V_H$, $C_L$ and CH1 domains; a F(ab)$_2$ fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody; a dAb fragment (Ward et al., 1989 Nature 341:544-546), which consists of a $V_H$ domain; and an isolated complementarity determining region (CDR).

Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., 1988 Science 242:423-426; and Huston et al., 1988 Proc. Natl. Acad. Sci. 85:5879-5883). Such single chain antibodies are also intended to be encompassed within the term "antigen-binding portion" of an antibody. These antibody fragments are obtained using conventional techniques known to those of skill in the art, and the fragments are screened for utility in the same manner as are intact antibodies.

An "isolated antibody", as used herein, refers to an antibody that is substantially free of other antibodies having different antigenic specificities (e.g., an isolated antibody that specifically binds a phosphorylated peptide is substantially free of antibodies that specifically bind antigens other than the phosphorylated peptide). An isolated antibody that specifically binds the phosphorylated peptide may, however, have cross-reactivity to other antigens, such as other proteins or peptides, which may or may not be phosphorylated. Moreover, an isolated antibody may be substantially free of other cellular material and/or chemicals.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human antibody", as used herein, is intended to include antibodies having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies of the invention may include amino acid residues not encoded by human sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

The term "human monoclonal antibody" refers to antibodies displaying a single binding specificity which have variable regions in which both the framework and CDR regions are derived from human sequences. In one embodiment, the human monoclonal antibodies are produced by a hybridoma which includes a B-cell obtained from a transgenic nonhuman animal, e.g., a transgenic mouse, having a genome comprising a human heavy chain transgene and a light chain transgene fused to an immortalized cell.

The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom; antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In certain embodiments, however, such recombinant human antibodies can be subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

As used herein, "isotype" refers to the antibody class (e.g., IgM, IgE, IgG such as IgG1 or IgG4) that is provided by the heavy chain constant region genes.

The phrases "an antibody recognizing an antigen" and "an antibody specific for an antigen" are used interchangeably herein with the term "an antibody which binds specifically to an antigen."

As used herein, an antibody that "specifically binds to a phosphorylated peptide" is intended to refer to an antibody that binds to a phosphorylated peptide with a $K_D$ of $5\times10^{-9}$ M or less, $2\times10^{-9}$ M or less, or $1\times10^{-1}$ M or less. An antibody that "cross-reacts with an antigen other a phosphorylated peptide" is intended to refer to an antibody that binds that antigen with a $K_D$ of $0.5\times10^{-8}$ M or less, $5\times10^{-9}$ M or less, or $2\times10^{-9}$ M or less. An antibody that "does not cross-react with a particular antigen" is intended to refer to an antibody that binds to that antigen, with a $K_D$ of $1.5\times10^{-8}$ M or greater, or a $K_D$ of $5–10\times10^{-8}$ M or $1\times10^{-7}$ M or greater. In certain embodiments, such antibodies that do not cross-react with the antigen exhibit essentially undetectable binding against these proteins in standard binding assays.

The term "$K_{assoc}$" or "$K_a$", as used herein, is intended to refer to the association rate of a particular antibody-antigen interaction, whereas the term "$K_{dis}$" or "$K_D$," as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e. $K_d/K_a$) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valence of both the antigen and antibody; and the structural arrangement of the interacting parts. Ultimately these factors define the specificity of the antibody, that is, the likelihood that the particular antibody is binding to a precise antigen epitope.

In order to get a higher avidity probe, a dimeric conjugate (two molecules of JWJ-1 coupled to a FACS marker) can be constructed, thus making low affinity interactions (such as with the germline antibody) more readily detected by FACS. In addition, another means to increase the avidity of antigen binding involves generating dimers or multimers of any of the fibronectin constructs described herein of the antibodies. Such multimers may be generated through covalent binding between individual modules, for example, by imitating the natural C-to-N-terminus binding or by imitating antibody dimers that are held together through their constant regions. The bonds engineered into the Fc/Fc interface may be covalent or non-covalent. In addition, dimerizing or multimerizing partners other than Fc can be used in hybrids to create such higher order structures.

As used herein, the term "Cross-reactivity" refers to an antibody or population of antibodies binding to epitopes on other antigens. This can be caused either by low avidity or specificity of the antibody or by multiple distinct antigens having identical or very similar epitopes. Cross reactivity is sometimes desirable when one wants general binding to a related group of antigens or when attempting cross-species labeling when the antigen epitope sequence is not highly conserved in evolution.

As used herein, the term "high affinity" for an IgG antibody refers to an antibody having a $K_D$ of $10^{-8}$ M or less, $10^{-9}$ M or less, or $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, or $10^{-8}$ M or less.

As used herein, the term "subject" includes any human or nonhuman animal. The term "nonhuman animal" includes all vertebrates, e.g., mammals and non-mammals, such as non-human primates, sheep, dogs, cats, horses, cows chickens, amphibians, reptiles, etc.

As used herein, the term, "optimized" means that a nucleotide sequence has been altered to encode an amino acid sequence using codons that are preferred in the production cell or organism, generally a eukaryotic cell, for example, a cell of *Pichia*, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in human cells, however optimized expression of these sequences in other eukaryotic cells is also envisioned herein. The amino acid sequences encoded by optimized nucleotide sequences are also referred to as optimized.

Standard assays to evaluate the binding ability of the antibodies toward phosphopeptides of various species are known in the art, including for example, ELISAs, western blots and RIAs. Suitable assays are described in detail in the Examples. The binding kinetics (e.g., binding affinity) of the antibodies also can be assessed by standard assays known in the art, such as by Biacore analysis. Assays to evaluate the effects of the antibodies on functional properties of phosphopeptides are described in further detail in the Examples.

Accordingly, an antibody that "inhibits" one or more of the phosphopeptides functional properties (e.g., biochemical, immunochemical, cellular, physiological or other biological activities, or the like) as determined according to methodologies known to the art and described herein, will be understood to relate to a statistically significant decrease in the particular activity relative to that seen in the absence of the antibody (e.g., or when a control antibody of irrelevant specificity is present). An antibody that inhibits the phosphopeptide activity effects such a statistically significant decrease by at least 10% of the measured parameter, by at least 50%, 80% or 90%, and in certain embodiments an antibody of the invention may inhibit greater than 95%, 98% or 99% of the phosphopeptide functional activity.

Homologous Antibodies

In yet another embodiment, an antibody of the invention may be may be 60%, 70%, 80%, 90%, 95%, 96%, 97%, 98% or 99% homologous to the antibodies described herein, and wherein the antibodies retain the desired functional properties of the anti-phosphopeptide antibodies of the invention.

As used herein, the percent homology between two amino acid sequences or two nucleotide sequences is equivalent to the percent identity between the two sequences. The percent identity between the two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two amino acid sequences can be determined using the algorithm of E. Meyers and W. Miller (Comput. Appl. Biosci., 4:11-17, 1988) which has been incorporated into the ALIGN program (version 2.0) using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package, using either a Blossom 62 matrix or a PAM250 matrix, and a gap weight of 16, 14, 12, 10, 8, 6, or 4 and a length weight of 1, 2, 3, 4, 5, or 6.

Additionally or alternatively, the protein sequences of the present invention can further be used as a "query sequence" to perform a search against public databases to, for example, identify related sequences. Such searches can be performed using the XBLAST program (version 2.0) of Altschul, et al., 1990 J. Mol. Biol. 215:403-10. BLAST protein searches can be performed with the XBLAST program, score=50, wordlength=3 to obtain amino acid sequences homologous to the antibody molecules of the invention. To obtain gapped alignments for comparison purposes, Gapped BLAST can be utilized as described in Altschul et al., 1997 Nucleic Acids Res. 25(17):3389-3402. When utilizing BLAST and Gapped BLAST programs, the default parameters of the respective programs (e.g., XBLAST and NBLAST) can be used.

Antibodies with Conservative Modifications

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis.

Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family, and the altered antibody can be tested for retained function using the functional assays described herein.

Engineered and Modified Antibodies

An antibody of the invention further can be prepared using an antibody of the invention herein as starting material to engineer a modified antibody, which modified antibody may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al., 1998 Nature 332:323-327; Jones, P. et al., 1986 Nature 321:522-525; Queen, C. et al., 1989 Proc. Natl. Acad. See. U.S.A. 86:10029-10033; U.S. Pat. No. 5,225,539 to winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database (available on the Internet at www.mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J. Immunol. 24:827-836; the contents of each of which are expressly incorporated herein by reference.

An example of framework sequences for use in the antibodies of the invention are those that are structurally similar to the framework sequences used by selected antibodies of the invention, e.g., consensus sequences and/or framework sequences used by monoclonal antibodies of the invention. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the $V_H$ and/or $V_L$ CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Engineered antibodies of the invention include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et at.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In yet other embodiments, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et at.

In another embodiment, one or more amino acid residues are altered to thereby alter the ability of the antibody to fix complement. This approach is described further in PCT Publication WO 94/29351 by Bodmer et at.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids. This approach is described further in PCT Publication WO 00/42072 by Presta. Moreover, the binding sites on human IgG1 for FcγR1, FcγRII, FcγRIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such a glycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, Lec13 cells, with reduced ability to attach fucose to Asn(297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta(1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Another modification of the antibodies herein that is contemplated by the invention is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the invention. See for example, EP 0 154 316 by Nishimura et al. and EP 0 401 384 by Ishikawa et al.

Methods of Engineering Antibodies

As discussed above, the anti-phosphopeptide antibodies can be used to create new anti-phosphopeptide antibodies by modifying full length heavy chain and/or light chain sequences, $V_H$ and/or $V_L$ sequences, or the constant region(s) attached thereto. Thus, in another aspect of the invention, the structural features of an anti-phosphopeptide antibody of the invention are used to create structurally related anti-phosphopeptide antibodies that retain at least one functional property of the antibodies of the invention.

The functional properties of the altered antibodies can be assessed using standard assays available in the art and/or described herein, such as those set forth in the Examples (e.g., ELISAs).

In certain embodiments of the methods of engineering antibodies of the invention, mutations can be introduced randomly or selectively along all or part of an anti-phosphopeptide antibody coding sequence and the resulting modified anti-phosphopeptide antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Immunoconjugates

In another aspect, the present invention features an anti-phosphopeptide antibody, or a fragment thereof, conjugated to a therapeutic moiety, such as a cytotoxin, a drug (e.g., an immunosuppressant) or a radiotoxin. Such conjugates are referred to herein as "immunoconjugates". Immunoconjugates that include one or more cytotoxins are referred to as "immunotoxins." A cytotoxin or cytotoxic agent includes any agent that is detrimental to (e.g., kills) cells. Examples include taxon, cytochalasin B, gramicidin D, ethidium bromide, emetine, mitomycin, etoposide, tenoposide, vincristine, vinblastine, t. colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), ablating agents (e.g., mechlorethamine, thioepa chloraxnbucil, meiphalan, carmustine (BSNU) and lomustine (CCNU), cyclothosphamide, busulfan, dibromomannitol, streptozotocin, mitomycin C, and cis-dichlorodiamine platinum (II) (DDP) cisplatin, anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Other examples of therapeutic cytotoxins that can be conjugated to an antibody of the invention include duocarmycins, calicheamicins, maytansines and auristatins, and derivatives thereof. An example of a calicheamicin antibody conjugate is commercially available (Mylotarg™; Wyeth-Ayerst).

Cytoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers. A linker can be chosen that is, for example, susceptible to cleavage by low pH within the lysosomal compartment or susceptible to cleavage by proteases, such as proteases preferentially expressed in tumor tissue such as cathepsins (e.g., cathepsins B, C, D).

For further discussion of types of cytotoxins, linkers and methods for conjugating therapeutic agents to antibodies, see also Saito, G. et al., 2003 Adv. Drug Deliv. Rev. 55:199-215; Trail, P. A. et al., 2003 Cancer Immunol. Immunother. 52:328-337; Payne, G., 2003 Cancer Cell 3:207-212; Allen, T. M., 2002 Nat. Rev. Cancer 2:750-763; Pastan, I. and Kreitman, R. J., 2002 Curr. Opin. Investig. Drugs 3:1089-1091; Senter, P. D. and Springer, C. J., 2001 Adv. Drug Deliv. Rev. 53:247-264.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$, and lutetium$^{177}$. Method for preparing radioimmunconjugates are established in the art. Examples of radioimmunoconjugates are commercially available, including Zevalin™ (DEC Pharmaceuticals) and Bexxar™ (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-γ; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et at., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev., 62:119-58 (1982).

Bispecific Molecules

In another aspect, the present invention features bispecific molecules comprising an anti-phosphopeptide antibody, or a fragment thereof, of the invention. An antibody of the invention, or antigen-binding portions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for the phosphopeptide and a second binding specificity for a second target epitope. For example, the second target epitope is an Fc receptor, e.g., human FcγR1 (CD64) or a human Fcα receptor (CD89). Therefore, the invention includes bispecific molecules capable of binding both to FcγR, FcαR or FcεR expressing effector cells (e.g., monocytes, macrophages or polymorphonuclear cells (PMNs), and to target cells expressing the phosphopeptide. These bispecific molecules target the phosphopeptide expressing cells to effector cell and trigger Fc receptor-mediated effector cell activities, such as phagocytosis of a cell expressing the phosphopeptide, antibody dependent cell-mediated cytotoxicity (ADCC), cytokine release, or generation of superoxide anion.

Additionally, for the invention in which the bispecific molecule is multi-specific, the molecule can further include a third binding specificity, in addition to an anti-Fc binding specificity and an anti-phosphopeptide binding specificity. For example, the third binding specificity could be an anti-enhancement factor (EF) portion, e.g., a molecule which binds to a surface protein involved in cytotoxic activity and thereby increases the immune response against the target cell. The "anti-enhancement factor portion" could be an antibody, functional antibody fragment or a ligand that binds to a given molecule, e.g., an antigen or a receptor, and thereby results in an enhancement of the effect of the binding determinants for the Fc receptor or target cell antigen.

The "anti-enhancement factor portion" can bind an Fc receptor or a target cell antigen. Alternatively, the anti-enhancement factor portion could bind to an entity that is different from the entity to which the first and second binding specificities bind. For example, the anti-enhancement factor portion can bind a cytotoxic T-cell (e.g. by CD2, CD3, CD8, CD28, CD4, CD44, ICAM-1 or other immune cell that results in an increased immune response against the target cell).

In one embodiment, the bispecific molecules of the invention comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

In one embodiment, the binding specificity for an Fcγ receptor is provided by a monoclonal antibody, the binding of which is not blocked by human immunoglobulin G (IgG). As used herein, the term "IgG receptor" refers to any of the eighty γ-chain genes located on chromosome 1. These genes encode a total of twelve transmembrane or soluble receptor isoforms which are grouped into three Fγ receptor classes: FcγRI (CD64), FcγRII(CD32), and FcγRIII (CD 16). In another embodiment, the Fcγ receptor is a human high affinity FcγRI. The human FcγRI is a 72 kDa molecule, which shows high affinity for monomeric IgG ($10^8$–$10^9$ $M^{-1}$).

The production and characterization of certain anti-Fcγ monoclonal antibodies are described by Fanger et at. in PCT Publication WO 88/00052 and in U.S. Pat. No. 4,954,617, the teachings of which are fully incorporated by reference herein. These antibodies bind to an epitope of FcγRI, FcγRII or FcγRIII at a site which is distinct from the Fcγ binding site of the receptor and, thus, their binding is not blocked substantially by physiological levels of IgG. Specific anti-FcγRI antibodies useful in this invention are mAb 22, mAb 32, mAb 44, mAb 62 and mAb 197. The hybridoma producing mAb 32 is available from the American Type Culture Collection, ATCC Accession No. HB9469. In other embodiments, the anti-Fcγ receptor antibody is a humanized form of monoclonal antibody 22 (H22). The production and characterization of the H22 antibody is described in Graziano, R. F. et al., 1995 J. Immunol 155 (10): 4996-5002 and PCT Publication WO 94/10332. The 1122 antibody producing cell line was deposited at the American Type Culture Collection under the designation HA022CL1 and has the accession no. CRL 11177.

In still other embodiments, the binding specificity for an Fc receptor is provided by an antibody that binds to a human IgA receptor, e.g., an Fc-alpha receptor (FcαRI (CD89), the binding of which does not have to be blocked by human immunoglobulin A (IgA). The term "IgA receptor" is intended to include the gene product of one a gene (FcαRI) located on chromosome 19. This gene is known to encode several alternatively spliced transmembrane isoforms of 55 to 110 kDa. FcαRI (CD89) is constitutively expressed on monocytes/macrophages, eosinophilic and neutrophilic granulocytes, but not on non-effector cell populations. FcαRI has an intermediate or medium affinity ($5 \times 10^7$ $M^{-1}$) for both IgA1 and IgA2, which is increased upon exposure to cytokines such as G-CSF or GM-CSF (Morton, H. C. et al., 1996 Critical Reviews in Immunology 116:423-440). Four FcαRI-specific monoclonal antibodies, identified as A3, A59, A62 and A77, which bind FcαRI outside the IgA ligand binding domain, have been described (Monteiro, R. C. et al., 1992 J. Immunol. 148:1764).

FcαRI and FcγRI are trigger receptors for use in the bispecific molecules of the invention because they are expressed primarily on immune effector cells, e.g., monocytes, PMNs, macrophages and dendritic cells; expressed at high levels (e.g., 5,000-100,000 per cell); mediators of cytotoxic activities (e.g., ADCC, phagocytosis); mediate enhanced antigen presentation of antigens, including self-antigens, targeted to them.

Other antibodies which can be employed in the bispecific molecules of the invention are murine, chimeric and humanized monoclonal antibodies.

The bispecific molecules of the present invention can be prepared by conjugating the constituent binding specificities, e.g., the anti-FcR and anti-phosphopeptide binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb×mAb, mAb×Fab, Fab×F(ab')$_2$ or ligand x Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. No. 5,260,203; U.S. Pat. No. 5,455,030; U.S. Pat. No. 4,881,175; U.S. Pat. No. 5,132,405; U.S. Pat. No. 5,091,513; U.S. Pat. No. 5,476,786; U.S. Pat. No. 5,013,653; U.S. Pat. No. 5,258,498; and U.S. Pat. No. 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest. For example, the FcR-antibody complexes can be detected using e.g., an enzyme-linked antibody or antibody fragment which recognizes and specifically binds to the antibody-FcR complexes. Alternatively, the complexes can be detected using any of a variety of other immunoassays. For example, the antibody can be radioactively 4 labeled and used in a radioimmunoassay (RIA) (see, for example, Weintraub; B., Principles of Radioimmunoassays, Seventh Training Course on Radioligand Assay Techniques, The Endocrine Society, March, 1986, which is incorporated by reference herein). The radioactive isotope can be detected by such means as the use of a γ counter or a scintillation counter or by autoradiography.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier. Such compositions may include one or a combination of (e.g., two or more different) antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. For example, the combination therapy can include an anti-phosphopeptide antibody of the present invention combined with at least one other anti-inflammatory or anti-osteoprotic agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. The carrier should be suitable for intravenous, intramuscular, subcutaneous, parenteral, spinal or epidermal administration (e.g., by injection or infusion). Depending on the route of administration, the active compound, i.e., antibody, immunoconjuage, or bispecific molecule, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al., 1977 J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as, aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, one can include isotonic agents, for example, sugars, polyalcohols such as mannitol, sorbitol, or sodium chloride in the composition. Prolonged absorption of the injectable compositions can be brought about by including in the composition an agent that delays absorption for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-phosphopeptide antibody of the invention include 1 mg/kg body weight or 3 mg/kg body weight by intravenous administration, with the antibody being given using one of the following dosing schedules: every four weeks for six dosages, then every three months; every three weeks; 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated or until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-phosphopeptide antibody of the invention can results in a decrease in severity of disease symptoms, an increase in frequency and duration of disease symptom-free periods, or a prevention of impairment or disability due to the disease affliction.

A composition of the present invention can be administered by one or more routes of administration using one or more of a variety of methods known in the art. As will be appreciated by the skilled artisan, the route and/or mode of administration will vary depending upon the desired results. Routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered by a nonparenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in one embodiment, a therapeutic composition of the invention can be administered with a needleless hypodermic injection device, such as the devices shown in U.S. Pat. No. 5,399,163; 5,383,851; 5,312,335; 5,064,413; 4,941,880; 4,790,824 or 4,596,556. Examples of well known implants and modules useful in the present invention include: U.S. Pat. No. 4,487,603, which shows an implantable micro-infusion pump for dispensing medication at a controlled rate; U.S. Pat. No. 4,486,194, which shows a therapeutic device for administering medicants through the skin; U.S. Pat. No. 4,447,233, which shows a medication infusion pump for delivering medication at a precise infusion rate; U.S. Pat. No. 4,447,224, which shows a variable flow implantable infusion apparatus for continuous drug delivery; U.S. Pat. No. 4,439,196, which shows an osmotic drug delivery system having multi-chamber compartments; and U.S. Pat. No. 4,475,196, which shows an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade, 1989 J. Cline Pharmacol. 29:685). Exemplary targeting moieties include folate or biotin (see, e.g., U.S. Pat. No. 5,416,016 to Low et al.); mannosides (Umezawa et al., 1988 Biochem. Biophys. Res. Commun. 153:1038); antibodies (P. G. Bloeman et al., 1995 FEBS Lett. 357:140; M. Owais et al., 1995 Antimicrob. Agents Chernother. 39:180); surfactant protein A receptor (Briscoe et al., 1995 Am. J. Physiol. 1233:134); p 120 (Schreier et al., 1994 J. Biol. Chem. 269:9090); see also K. Keinanen; M. L. Laukkanen, 1994 FEBS Lett. 346:123; J. J. Killion; I. J. Fidler, 1994 Imrnunomethods 4:273.

Uses and Methods of the Invention

The antibodies (and immunoconjugates and bispecific molecules) of the present invention have in vitro and in vivo diagnostic and therapeutic utilities. For example, these molecules can be administered to cells in culture, e.g. in vitro or in vivo, or in a subject, e.g., in vivo, to treat, prevent or diagnose a variety of disorders. The term "subject" as used herein in intended to include human and non-human animals. Non-human animals includes all vertebrates, e.g., mammals and non-mammals, such as non-human primates, sheep, dogs, cats, cows, horses, chickens, amphibians, and reptiles. When antibodies to the phosphopeptide are administered together with another agent, the two can be administered in either order or simultaneously.

In one embodiment, the antibodies (and immunoconjugates and bispecific molecules) of the invention can be used to detect levels of the phosphopeptide, or levels of cells that contain the phosphopeptide. This can be achieved, for example, by contacting a sample (such as an in vitro sample) and a control sample with the anti-phosphopeptide antibody under conditions that allow for the formation of a complex between the antibody and the phosphopeptide. Any complexes formed between the antibody and the phosphopeptide are detected and compared in the sample and the control. For example, standard detection methods, well known in the art, such as ELISA and flow cytometric assays, can be performed using the compositions of the invention.

Accordingly, in one aspect, the invention further provides methods for detecting the presence of the phosphopeptide (e.g., human the phosphopeptide antigen) in a sample, or measuring the amount of the phosphopeptide, comprising contacting the sample, and a control sample, with an antibody of the invention, or an antigen binding portion thereof, which specifically binds to the phosphopeptide, under conditions that allow for formation of a complex between the antibody or portion thereof and the phosphopeptide. The formation of a complex is then detected, wherein a difference in complex formation between the sample compared to the control sample is indicative of the presence of the phosphopeptide in the sample.

Microarrays

An aspect of the present invention provides herein articles of manufacture, such as arrays, comprising the compilations, or sets, libraries or collections, of phosphopeptides and anti-phosphopeptide antibodies of the invention. The terms "array" or "microarray" or "chip" or "biochip" as used herein is a plurality of target elements, each target element having a defined amount of one or more biological molecules, e.g., phosphopeptides and anti-phosphopeptide antibodies, immobilized on a defined location on a substrate surface; as described in further detail, below. Making and using the compilations, or sets, libraries or collections, of phosphopeptide and anti-phosphopeptide antibody arrays and practicing the methods of the present invention can incorporate any known "array," also referred to as a "microarray" or "biochip," or variation thereof.

Arrays are generically a plurality of "target elements," or "spots," each target element having a defined amount of one or more biological molecules, e.g., phosphopeptides and anti-phosphopeptide antibodies, immobilized on a defined location on a substrate surface. Typically, the immobilized biological molecules are contacted with a sample for specific binding, e.g., hybridization, between molecules in the sample and the array. Immobilized target elements can contain reference sequences, such as positive and negative controls, and the like.

The target elements of the arrays may be arranged on the substrate surface at different sizes and different densities. Different target elements of the arrays can have the same molecular species, but, at different amounts, densities, sizes, labeled or unlabeled, and the like. The target element sizes and densities will depend upon a number of factors, such as the nature of the label (the immobilized molecule can also be labeled), the substrate support (it is solid, semi-solid, fibrous, capillary or porous), and the like.

Each target element may have substantially the same phosphopeptides and anti-phosphopeptide antibodies. Thus, for example, a target element may contain more than one phosphopeptide or anti-phosphopeptide antibody, and each may be broken into fragments of different lengths, as described herein. The length and complexity of the phosphopeptide or anti-phosphopeptide antibody fixed onto the array surface is not critical to the invention.

The array can have phosphopeptides or anti-phosphopeptide antibodies immobilized on any substrate, e.g., a solid surface (e.g., nitrocellulose, glass, quartz, fused silica, plastics and the like). See, e.g., U.S. Pat. No. 6,063,338 describing multi-well platforms comprising cycloolefin polymers if fluorescence is to be measured. Arrays used in the methods of the invention can include housing having components for controlling humidity and temperature during the hybridization and wash reactions.

In making and using the compilations, or sets, libraries or collections, of phosphopeptide or anti-phosphopeptide antibody arrays and practicing the methods of the invention, known arrays and methods of making and using arrays can be incorporated in whole or in part, or variations thereof, as described, for example, in U.S. Pat. Nos. 6,277,628; 6,277,489; 6,261,776; 6,258,606; 6,054,270; 6,048,695; 6,045,996; 6,022,963; 6,013,440; 5,965,452; 5,959,098; 5,856,174; 5,830,645; 5,770,456; 5,632,957; 5,556,752; 5,143,854; 5,807,522; 5,800,992; 5,744,305; 5,700,637; 5,556,752; 5,434,049; see also, e.g., WO 99/51773; WO 99/09217; WO 97/46313; WO 96/17958; see also, e.g., Johnston (1998) Curr. Biol. 8:R171-R174; Schummer (1997) Biotechniques 23:1087-1092; Kern (1997) Biotechniques 23:120-124; Solinas-Toldo (1997) Genes, Chromosomes & Cancer 20:399-407; Bowtell (1999) Nature Genetics Supp. 21:25-32. See also published U.S. patent applications Nos. 20010018642; 20010019827; 20010016322; 20010014449; 20010014448; 20010012537; 20010008765. The present invention can use any known array, e.g., GeneChips™, Affymetrix, Santa Clara, Calif.; SPECTRALCHIP™ Mouse BAC Arrays, SPECTRALCHIP™ Human BAC Arrays and Custom Arrays of Spectral Genomics, Houston, Tex., and their accompanying manufacturer's instructions.

The invention having been fully described, it is further illustrated by the following examples and claims, which are illustrative and are not meant to be further limiting. Those skilled in the art will recognize or be able to ascertain using no more than routine experimentation, numerous equivalents to the specific procedures described herein. Such equivalents are within the scope of the present invention and claims. The contents of all references, including issued patents and published patent applications, cited throughout this application are hereby incorporated by reference.

EXAMPLES

Additional embodiments and supporting data including sequences obtained by the methods herein are found in: Villen et al. (Large-scale phosphorylation analysis of mouse liver. Proc Natl Acad Sci U S A. 104:1488-1493, 2007); Li et al. (Large-scale phosphorylation analysis of alpha-factor-arrested *Saccharomyces cerevisiae*. J Proteome Res. 6:1190-1197, 2007); Bakalarski et al. (The effects of mass accuracy, data acquisition speed, and search algorithm choice on peptide identification rates in phosphoproteomics. Anal Bioanal Chem, 2007, accepted for publication and available online); Haas et al. (Optimization and use of peptide mass measurement accuracy in shotgun proteomics. Mol Cell Proteomics. 5:1326-1337, 2006); Beausoleil et al. (A probability-based approach for high-throughput protein phosphorylation analysis and site localization. Nat Biotechnol. 24:1285-1292, 2006); Ballif et al. (Identification of 14-3-3 epsilon substrates from embryonic murine brain. J Proteome Res. 5:2372-2379, 2006); and Elias et al. (Target-decoy search strategy for increased confidence in large-scale protein identifications by mass spectrometry. Nat Methods. 4:207-214, 2007). The contents of each of these references is incorporated by reference in its entirety herein.

Example 1

Generation of a Phosphorylation Repertoire by Mass Spectrometry

An overview of an embodiment of a method of the present invention is provided in FIG. 1. In detail, Liver tissue from a 21-day-old mouse was lysed, and 10 mg of the resulting liver protein were digested with trypsin.

In a typical large-scale phosphorylation analysis, a preliminary enrichment step of phosphopeptides is used to reduce sample complexity and increase the relative concentration. A wide variety of phosphopeptide enrichment strategies can be used, including, for example, chemical approaches such as beta-elimination or phosphoramidate chemistry (Oda et al., 2001; Tao et al., 2005; Zhou et al., 2001), peptide immunoprecipitation with phospho-specific motif antibodies (Rush et al., 2005), affinity purification through metal complexation with the phosphate group (IMAC) (Ficarro et al., 2002), solution charge-based enrichment by strong cation exchange (SCX) chromatography (Beausoleil et al., 2004) and combinations of these (Gruhler et al., 2005; Zhang et al., 2005).

In the present example, the resulting trypsin digested peptides from the mouse liver were subjected to a two-step phosphopeptide enrichment procedure (FIG. 1 panel A) consisting of strong cation exchange (SCX) chromatography with fraction collection followed by immobilized metal ion affinity chromatography (IMAC).

SCX chromatography separates primarily based on solution charge state. At pH 2.7, substantial enrichment in early eluting fractions due to the presence of an additional negative charge provided by the phosphate group was obtained (Ballif et al., 2004; Beausoleil et al., 2004). In addition, a general separation of tryptic peptides is achieved.

Figure 2:
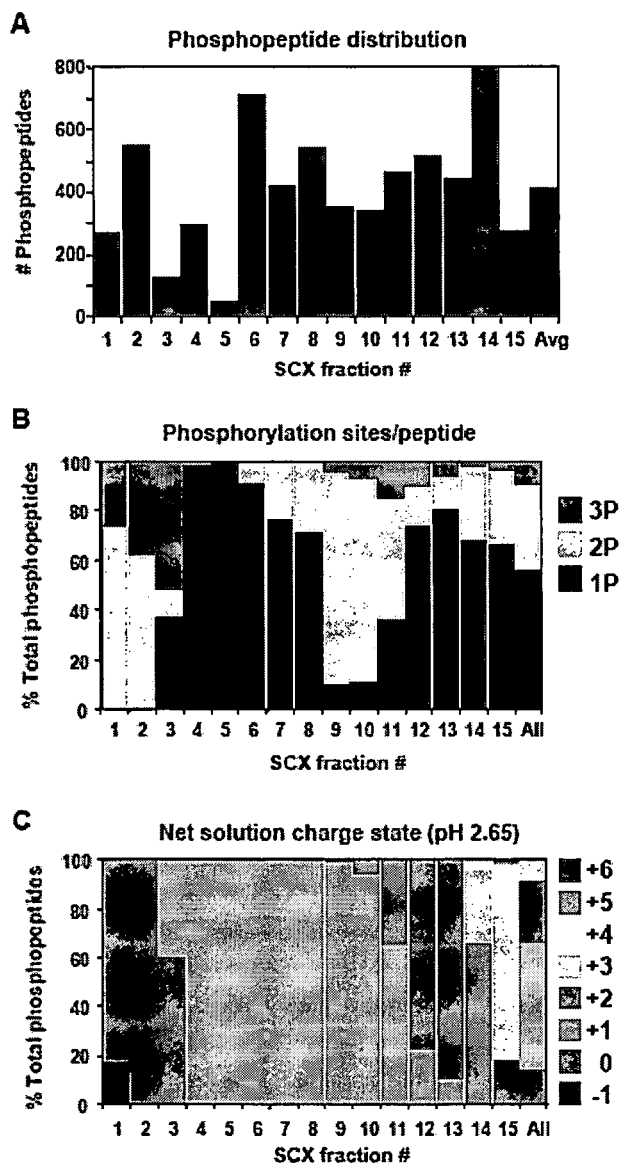
FIG. 2 is a set of bar graphs that show distributions of phosphopeptides and their properties obtained in each of 15 fractions isolated from a strong cation exchange (SCX) chromatography system.

Fractions (15) were collected along an SCX gradient expanded in the +1 charge state region, where a significant portion of phosphopeptides were eluted (Beausoleil et al., 2004). As shown in FIG. 2 panel A, each SCX fraction averaged more than 400 phosphopeptide identifications which were primarily separated by solution charge state (FIG. 2 panel C). The number of phosphates per peptide was periodic (FIG. 2 panel B) due to the strong retention effect of each additional basic residue (arginine, lysine or histidine). The 2-step purification successfully provided samples with over 90% phosphopeptides relative to total peptide sequences.

Each fraction was then subjected to immobilized metal ion affinity chromatography (IMAC). IMAC has also been shown to provide exceptional enrichment of phosphopeptides (Ficarro et al., 2002; Gruhler et al., 2005).

Following IMAC enrichment, each fraction was analyzed by microcapillary liquid-chromatography coupled on-line to tandem mass spectrometry (LC-MS/MS) in the form of a hybrid linear ion trap/Fourier transform ion cyclotron resonance (FTICR) mass spectrometer.

Fourier transform mass spectrometry (Fourier transform ion cyclotron resonance MS), measures mass by detecting the image current produced by ions cyclotroning in the presence of a magnetic field. Instead of measuring the deflection of ions with a detector such as a electron multiplier, the ions are injected into a Penning trap (a static electric/magnetic ion trap) where they effectively form part of a circuit. Detectors at fixed positions in space measure the electrical signal of ions which pass near them over time producing cyclical signal. Since the frequency of an ion's cycling is determined by its mass to charge ratio, this can be deconvoluted by performing a Fourier transform on the signal. FTMS has the advantage of high sensitivity (since each ion is 'counted' more than once) and much high resolution and thus precision.

Tandem mass spectrometry involves multiple steps of mass selection or analysis, usually separated by some form of fragmentation. A tandem mass spectrometer is one capable of multiple rounds of mass spectrometry. For example, one mass analyzer can isolate one peptide from many entering a mass spectrometer. A second mass analyzer then stabilizes the peptide ions while they collide with a gas, causing them to fragment by collision-induced dissociation (CID). A third mass analyzer then catalogs the fragments produced from the peptides.

There are various methods for fragmenting molecules for tandem MS, including for example, collision-activated dissociation (CAD), collision-induced dissociation (CID), electron capture dissociation (ECD), electron transfer dissociation (ETD), infrared multiphoton dissociation (IRMPD) and blackbody infrared radiative dissociation (BIRD). An important application using tandem mass spectrometry is in protein identification.

In the present example, high mass accuracy precursor ions were collected as FTICR master spectra, and more than 77,000 MS/MS spectra were generated by collision-activated dissociation (CAD) in the linear ion trap.

These MS/MS spectra were searched against a composite database of mouse proteins containing sequences in first the forward and then the reverse direction (FIG. 1 panel B). This target/decoy database strategy permits a false-positive (FP) rate to be estimated based on the number of reversed-sequence identifications populating the final data set (Elias et al., 2005; Peng et al., 2003). Orthogonal filtering criteria, such as mass accuracy, tryptic state, solution charge state and Sequest scoring were utilized to establish a final data set with 8,527 phosphopeptides from 2,149 proteins identified at a FP rate of 0.02% (only two reverse-sequence matches were contained within the final peptide list). These peptides contained 5,250 nonredundant phosphorylation sites.

Example 2

Generation of Phosphopeptides Using the Method of the Present Invention from a Single Protein, Lipolysis Stimulated Receptor (LSR)

Lipolysis stimulated receptor mRNA is abundant in liver, and the protein is thought to be involved in the clearance of triglyceride-rich lipoproteins (Yen et al., 1999). An LSR−/− mouse is embryonic lethal between E12.5 and E15.5. It was found that E14.5 embryo livers were much smaller than those of wild-type littermates, indicating that the expression of LSR is important for liver and embryonic development (Mesli et al., 2004).

As an example, Table 1 displays six phosphopeptides (SEQ ID NOs: 26-31) identified from a single protein, lipolysis stimulated receptor (LSR) from implementation of the method of the current invention. Although a total of twenty-three redundant phosphopeptides were detected for LSR, all 12 non-redundant sites were contained within this set of six phosphopeptides.

Figure 3:
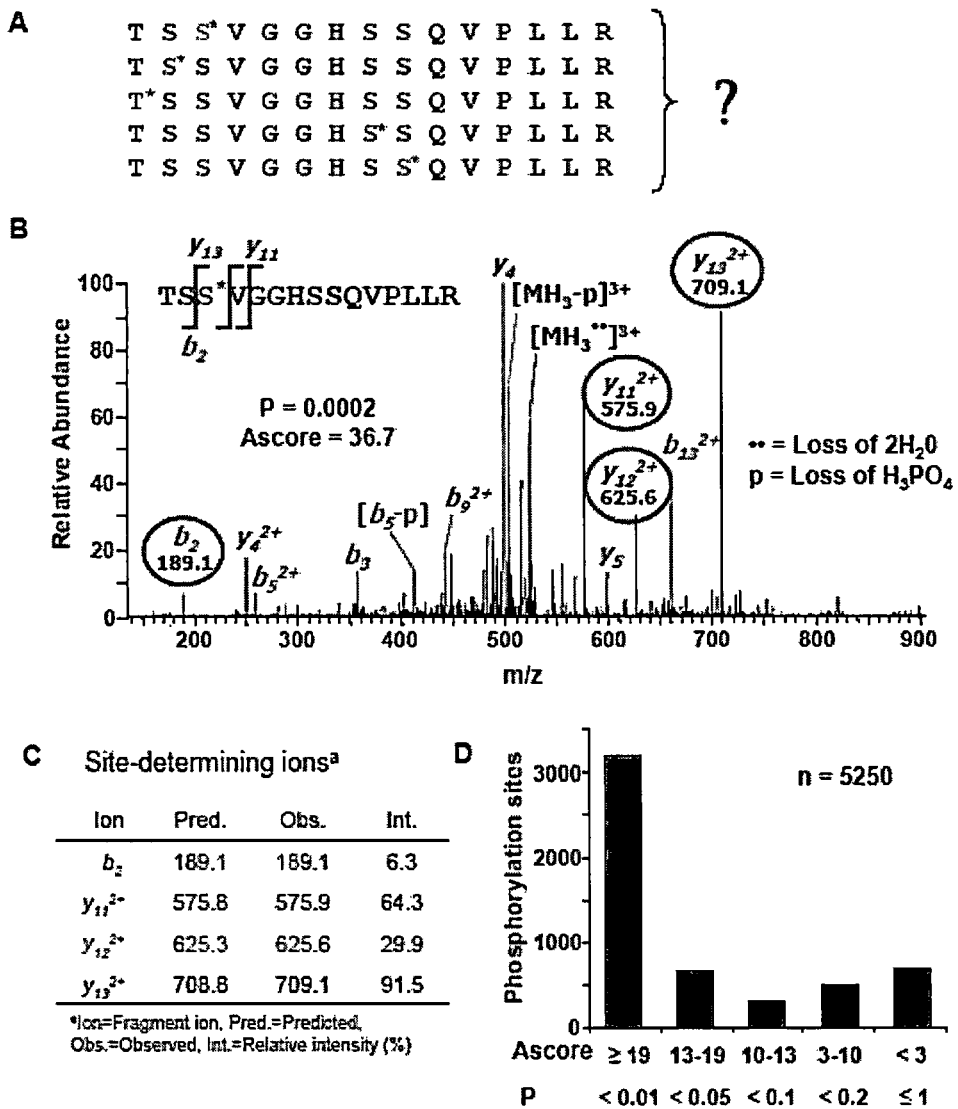
FIG. 3 is a drawing showing a strategy for assessing correct phosphorylation site localization.

LSR was highly phosphorylated and contained sites primarily suggestive of basophilic kinases (Rxxs), but also had acidiphilic (sxxE) and proline-directed (sP) phosphorylation. In addition, two phosphorylation sites were found near the C terminus. All 12 sites were localized to the cytoplasmic side of the transmembrane domain.

dissociation. These fragment ions are "site-determining" in that their detection distinguishes between two likely, often immediately adjacent acceptor residues (FIG. 3 panel C). If ions at the critical m/z values are present due to chance or not detected at all, then phosphorylation site placement should be considered ambiguous.

In the past, subjective manual validation has been performed to inspect raw data for the presence or absence of site-determining ions, i.e., ambiguity assessment, for each phosphopeptide result.

The present invention provides a probability-based algorithm that scans for site-determining ions and computes the likelihood of their detection by chance alone, allowing all possible site placements to be considered (the Ascore algorithm; Beausoleil et al., 2006). Ascore values directly represent the probability (P) of detection due to chance as $-10 \times \log(P)$, with scores >19 corresponding to sites localized with near certainty (P<0.01).

In the example in FIG. 3 panel B, the phosphorylation site was considered correctly localized because the presence of several site-determining ions produced an Ascore of 36.7 (P=0.0002). An Ascore value was calculated for every site from the 8,527 phosphopeptides. The score distribution for all accepted 5,250 non-redundant sites is shown in FIG. 3 panel D.

TABLE 1

Example of phosphorylation sites and phosphopeptides identified from a single protein, lipolysis-stimulated receptor (LSR). This protein is also called Lisch7 (liver-specific bHLH-zip transcription factor) in the database.

| Phosphorylation sites[a] | SEQ ID NOs | Peptide[b] | # sites | m/z | Mass error (ppm)[c] | Charge state | XCorr[d] | Literature[e] |
|---|---|---|---|---|---|---|---|---|
| S308, S313 | 26 | (R) TSS*VGGHS*SQVPLLR | 2 | 842.8795 | 4.1 | 2 | 2.127 | None |
| S375, S379 | 27 | (R) AMS*EVTS*LHEDDWR | 2 | 926.3401 | 4.2 | 2 | 2.445 | None |
| S407 | 28 | (R) APALTPIRDEEWNRHS*PR | 1 | 742.3697 | 15.3 | 3 | 2.351 | None |
| S436, S448, S451, S459 | 29 | (R) S*VDALDDINRPGS*TES*GRSSPPSS*GR | 4 | 988.7249 | 13.4 | 3 | 2.906 | None |
| S473 | 30 | (R) SRS*RDDLYDPDDPR | 1 | 893.8841 | 12.4 | 2 | 2.651 | None |
| S588, S591 | 31 | (K) NLALS*RES*LVV- | 2 | 680.8219 | 7.1 | 2 | 2.234 | Yes[f] |

[a]Phosphorylation sites were localized with the Ascore method (Beausoleil et al., 2006). Sites with <99% certainties of correct site placement are underlined.
[b]Twelve sites on 23 redundant tryptic peptides were actually detected from this protein (See Supplementary Table 1). For space reasons, the minimal set of peptides (6) is shown for the 12 detected sites. Phosphorylation sites are designated by an asterisk, all methionines were detected in their oxidized form, and the C terminus of the protein is designated with a "-". Additional residues from the database are shown within parentheses and help to visualize motifs (e.g., Rxxs).
[c]ppm (part-per-million) mass accuracy values were not recalibrated.
[d]XCorr values were from the Sequest algorithm.
[e]Known sites were extracted from the Phosphosite (www.phosphosite.org) and Phospho.ELM (http://phospho.elm.eu.org) databases.
[f](Kim et al., 2005)
[g]The peptides shown above in Table 1 have SEQ ID NOs: 26-31.

Example 3

Assessing the Certainty of Precise Site Localization for 5,250 Detected Sites

Database searching programs are well-suited to peptide sequence identification but can fail to correctly position a site of post-translational modification, in particular when multiple acceptor residues (serines, threonines, and/or tyrosines in the case of phosphorylation) occur in very close sequence proximity (FIG. 3 panel A).

For each phosphopeptide, there is a subset of b- and y-type fragment ions (amide bond breakages) that occur after the phosphopeptides has been subjected to collision-activated Example 4

Positional Analysis of Phosphorylation Sites in Proteins

Without being bound by any particular theory or mechanism of action, it is believed that phosphorylation is more likely to occur in flexible and exposed regions of a protein.

Figure 4:
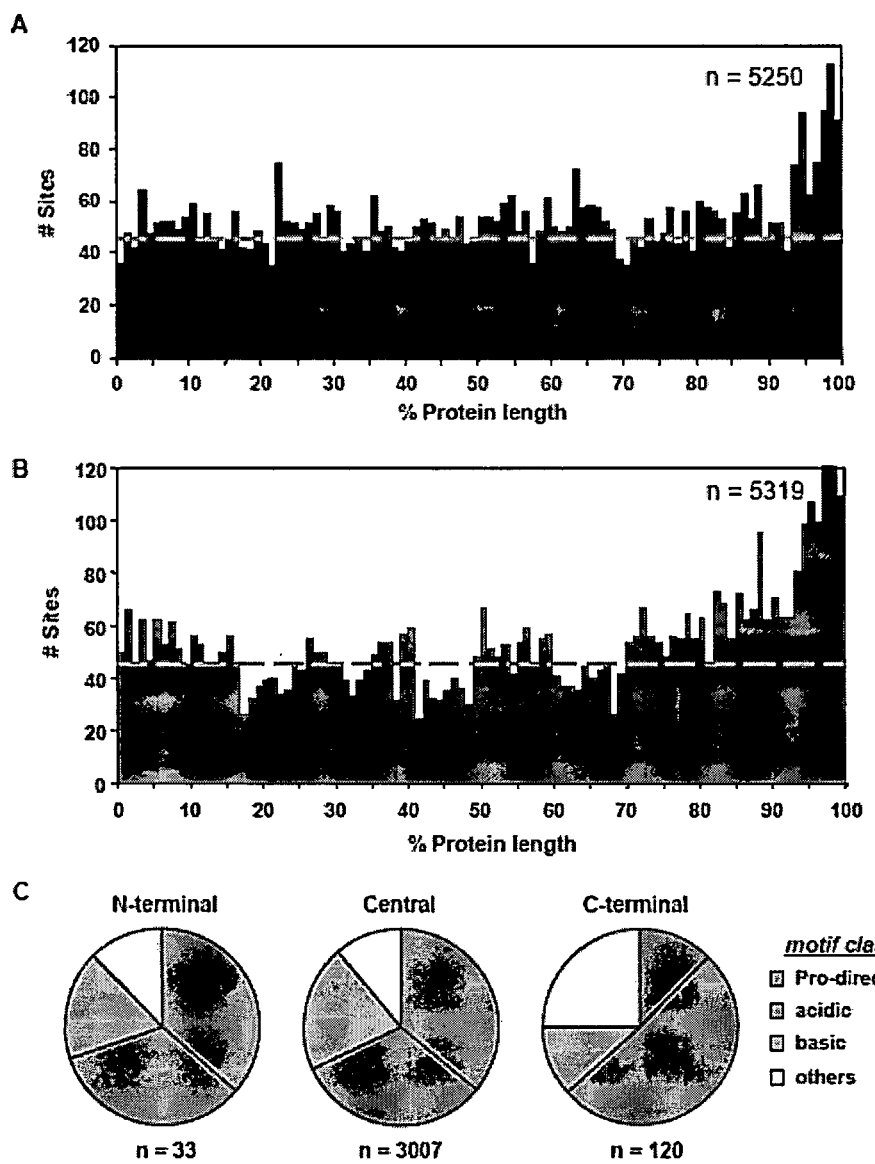
FIG. 4 is a set of graphs showing positional distribution of phosphorylation sites.

Analysis of the position of phosphorylation sites along the protein sequences was performed by dividing the protein length into 1% bins and counting the number of sites within each division. As shown in FIG. 4 panel A, a substantial number of sites fell into the two last bins, i.e., phosphorylation events located at 98-100% of the protein's length. In fact, more than a 2.5-fold increase in the number of phosphorylation sites was observed in this C-terminal region.

However, a similar trend was not observed for bins near the N terminus. In order to account for all possible versions of N-terminal peptides, additional searches with N-terminal acetylation were performed also permitting cleavage of the initial methionine residue. Even considering all four possibilities for each N terminus (included in FIG. 4 panel A), the frequency of phosphorylation at the extreme N terminus of a protein was very similar to the central regions of the protein and distinctly different from what was obtained for the C terminus. Moreover, this C-terminal preference was not specific to being acquired using our methodology, as the same distribution was obtained from plotting the complete contents of the Phospho.ELM database, which is similar in size to our data set (FIG. 4 panel B).

The Ser/Thr protein kinases fall into three major subgroups—proline-directed, basophilic and acidiphilic on the basis of the types of substrate sequences preferred (Pinna and Ruzzene, 1996). In order to better understand the classes of kinases involved in these positional effects, all localized phosphorylation sites were organized into three general sequence categories.

While the pattern of sequence category frequencies for phosphorylation sites within the first 10 residues of a protein's sequence were identical to central sites, phosphorylation events within the final 10 residues were dramatically different. Proline-directed phosphorylation was greatly reduced at the C terminus, and acidic motifs were increased (FIG. 4 panel C). An increase in acidic motifs might be explained if the C-terminal carboxylic acid itself was recognized by kinases preferring series of glutamic and aspartic acid residues. An example of this is found for the C terminus of LSR protein in Table 1. Finally, a control utilizing and classifying all serines and threonines from these proteins did not show a distinct sequence category distribution for C-terminal positions.

Without being bound by any particular theory or mechanism of action, it is believed that these results may have implications for protein tagging examples where specific epitope tags are incorporated into the sequence of proteins, often at the C terminus (Rigaut et al., 1999). It is possible that C-terminal phosphorylation events would not occur or be reduced under these conditions and therefore influence interactions with other proteins and protein function.

Example 5

Correlation of General Phosphorylation Motifs with Cellular Localization and Protein Function To investigate if different cellular compartments, protein functions, or biological processes might exhibit unusual or even idiosyncratic phosphorylation patterns, correlations between Gene Ontology (GO) annotation categories and phosphopeptide sequence characteristics were examined in our complete list of 2,149 phosphoproteins (FIG. 8).

Figure 5:
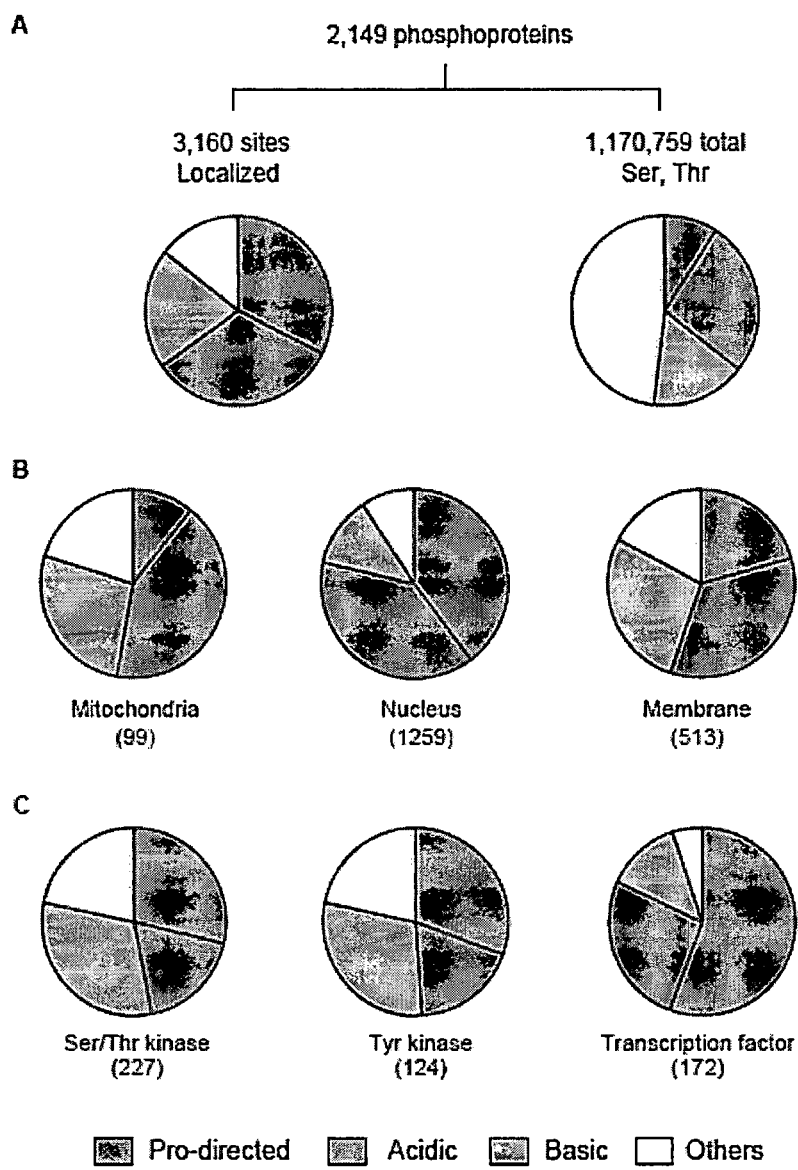
FIG. 5 is a set of pie graphs showing classification of phosphorylation sites into the three most-general kinase recognition sequence categories: acidic, basic, proline-directed, and others. The pie graphs in FIG. 5 panel A show a comparison of sequence category distributions for the sites detected in this study with the control set of all serine and threonine residues from the same set of proteins. The pie graphs in FIG. 5 panel B show diverse phosphorylation patterns for proteins in different gene ontology annotation cellular localization categories. The pie graphs in FIG. 5 panel C show general phosphorylation kinase classification patterns for each of three functional gene ontology categories.

FIG. 5 panel A shows the distribution of localized sites from 2,149 proteins within each of three general motif classes. As a control, the background frequencies for serines and threonines from these proteins are also shown. From these data, most phosphoserine and phosphothreonine-containing sites (85%) were classified: prolinedirected (32%), acidic (33%) and basic (20%).

Minor variations in the distribution of sites for the four sequence categories were observed between GO classes using a background of all serines and threonines (FIG. 8 panel B). In contrast, dramatic differences were found in the distributions for observed phosphorylation sites for both cellular location (FIG. 5 panel B and FIG. 8 panel A) and cellular function or process (FIG. 5 panel C and FIG. 8 panel A).

For example, acidic phosphorylated sequences were frequently observed in extracellular and mitochondrial proteins but found less often in cytoskeletal proteins. Basic phosphorylated sequences were rarely found in nuclear proteins, but were abundant in membrane, mitochondrial, and cytoskeletal proteins. Furthermore, proline-directed phosphorylation events occurred with high frequency in proteins in the nucleus where many proline-directed kinases are located, such as many CDK family members, but not in mitochondria or in the extracellular environment (FIG. 5 panel B, FIG. 8).

The same frequency distribution of general kinase categories was observed for serine/threonine kinases and tyrosine kinases (FIG. 5 panel C), suggesting that kinase autophosphorylation may represent only one of many components in their overall regulation and is commonly accompanied by transphosphorylation of other kinases.

Proteins involved in protein phosphorylation, signal transduction and signaling cascades exhibited a distinct distribution with a low frequency of acidic phosphorylated sequences and higher numbers of basic sequences (FIG. 8 panel A). Transcription factors showed a characteristic signature with a strong preference for phosphorylation at proline-directed sites and very low numbers of basic sites (FIG. 5 panel C). Conversely, low numbers of proline-directed events were discovered in proteins involved in metabolism, electron transport and those with oxidoreductase activity (FIG. 8 panel A).

Example 6

Phosphorylation Motif Discovery

After phosphopeptides in our data set were generally classified into three primary sequence categories, these categories were further refined into specific, frequency-corrected phosphorylation motifs. Peptide sequences for phosphorylation sites localized with >99% confidence (2795 pSer, 339 pThr and 26 Tyr) were all aligned, and their lengths were adjusted to ±6 amino acids from the central position and submitted to the Motif-X algorithm (Schwartz and Gygi, 2005). Table 2 lists the motifs generated containing a minimum of 50 phosphoserine (~2% of the total) and 6 phosphothreonine occurrences.

TABLE 2

Analysis of single and double phosphorylation motifs using the Motif-X algorithm.

| SEQ ID NOs | Motif[a,b] | Literature[c] | #Occ[d] |
|---|---|---|---|
| | Serine motifs | | |
| 4 | ...R..sP..... | | 126 |
| 32 | ....P.sP..... | MAP kinase | 159 |
| 5 | ..SP..sP..... | | 51 |
| 6 | ......sP....R | | 66 |
| 33 | ......sD.E.E. | CK2 | 56 |
| 34 | ......sPR.... | Growth-associated histone HI | 55 |
| 35 | ...RR.s...... | PKA | 107 |
| 36 | ......s..EE.. | CK2 | 118 |
| 3 | ......sP..... | Proline-directed | 423 |
| 37 | .L.R..s...... | CaM kinase and PKD | 69 |
| 38 | ......sD.E... | CK2 | 83 |
| 39 | ......sD.D... | CK2 | 92 |

TABLE 2-continued

Analysis of single and double phosphorylation motifs using the Motif-X algorithm.

| SEQ ID NOs | Motif[a,b] | Literature[c] | #Occ[d] |
|---|---|---|---|
| 40 | .R.R..s...... | Akt kinase | 59 |
| 41 | ......sEE.... | CK2 | 60 |
| 1 | ...R..s....... | PKA and PKC | 198 |
| 7 | R..S..s...... | | 50 |
| 42 | ......s.D.... | CK2 | 164 |
| 43 | ......s..E.... | CK2 | 133 |
| 44 | .....Ds...... | CK2-like | 86 |
| 45 | ......s...D... | CK2 | 69 |
| 46 | ....R.s...... | PKA and PKC | 71 |
| 2 | ......s..E... | CK2 | 60 |
| 8 | ......s...S... | | 86 |
| Threonine motifs | | | |
| 9 | ......tPP.... | | 45 |
| 47 | ....P.tP..... | MAP kinase | 39 |
| 48 | ......tP..... | Pro-directed | 105 |
| 49 | ......tD.E... | CK2 | 16 |
| 50 | ...R..t...... | PKA | 22 |
| Double-phosphoryation motifs | | | |
| 10 | ..sP..sP..... | | 37 |
| 11 | ....sPsP..... | | 23 |
| 12 | ......sDsE... | | 24 |
| 13 | ......ss.EE.. | | 24 |
| 14 | ......sP.s... | | 24 |
| 15 | ....s.sE.E... | | 22 |
| 11 | ......sPsP... | KIS kinase | 23 |
| 16 | ..s...sP..... | | 20 |
| 17 | .....ss..E.... | | 33 |
| 18 | ...R..s..s... | | 27 |
| 19 | ...s..s..E... | | 27 |
| 20 | ....s.sE..... | | 20 |
| 21 | ...R..s..s.... | | 24 |
| 51 | ......ss..E.. | | 21 |
| 22 | ......ss...D. | | 22 |
| 8 | ......s...s... | CK1 | 54 |
| 23 | ...s...sL..... | | 22 |
| 52 | ......s...s.. | GSK3 | 46 |

[a]Parameters included $10^{-6}$ significance and a number of occurrences depending on the size of each data set: 50 occurrences for single pSer. 6 for pThr and 20 for the double-phosphorylation motifs centered at Ser.
[b]Lowercase "s" and "t", represents phosphorylated Ser and Thr, respectively. A "." denotes any amino acid.
[c]Kinase is listed if described in the literature.
[d]#Occ is the number of occurrences.

To display each identified motif graphically, logo-like representations were created. These logos included not only the residues strictly discovered to be part of the motif (Table 2), but also the frequencies of additional adjacent amino acids (FIG. 6). Certain motifs are commonly associated with specific kinases (Peri et al., 2004) and were prevalent in our data set. Basophilic kinase motifs such as RRxs (PKA), LxRxxs (CaM kinase family), and RxRxxs were identified. The latter has been associated with Akt or Akt-like kinase activity (Alessi et al., 1996). 88 sites with this motif were found, including known Akt substrates (e.g., IRS1, ACINUS, CAHSP24). New potential substrates included SNIP1, CoREST, NDRG1, NDRG2, and NDRG3.

In addition, several acidic Casein Kinase II motifs (sxDxExE, sxxEE, sDxE, sDxD, etc) and prolinedirected motifs recognized by MAP kinase (PxsP and PxtP) were well represented in the data with substrates including MAPK2 and several Rsk family members.

Also identified were populations of peptides containing motifs that have not as yet been associated with a particular kinase. For example, there is no known kinase or interaction domain that specifically targets tPP sequences. This motif was frequently observed in our current data set (45 occurrences). It is possible that the second proline could modulate kinase activity of a known proline-directed kinase. Other examples of identified motifs were RxxsP and SPxxsP with 126 and 51 occurrences, respectively. The latter could be a priming site for future GSK-3 phosphorylation at the +4 position.

Fewer motifs were found for phosphothreonine, as the total number of phosphorylation events identified on this residue was significantly less than for serine. The lack of statistical representation for phosphotyrosine precluded the generation of significant motifs for that residue with only 26 phosphotyrosine sites identified.

One class of undescribed motif was identified which exhibited properties of both acidic and basic motifs, i.e., a "dipolar" motif, containing the minimum consensus sequence Rxxsxx[DE]. In addition to the locked positions, most of the residues on the amino terminal side of the phosphoserine are basic in nature, (K or R), while acidic (D and E) residues are abundant on the C-terminal half.

The Phospho.ELM database contains 109 (47 with D and 72 with E) instances of such motifs, with associated kinases for 67 of them, usually directed to basic motifs. PKA was reported responsible for 21 sites, PKC and Akt for 6, and CaM-II for 5. Those sequences associated to acidic kinases were represented almost uniquely by 9 sites assigned to CK2.

However, this motif was not extracted when the Phospho.ELM database was run with Motif-X. Logo representations for these sequences were similar, but not exact (FIG. 9). Moreover, out of 125 sites with the dipolar motif identified in this study only 5 (4%) had been reported in the Phospho.ELM database. For 2 of these, PKA was the assigned kinase.

Without being bound by any particular theory or mechanism of action, it is envisioned that some sites have evolved to respond to both acidiphilic and basophilic kinases.

Example 7

Multiple Phosphorylations in a Short and Defined Distance: Double Phosphorylation Motifs In this study, 39% of the phosphopeptides identified were found to be multiply phosphorylated. This motif class constitutes the basis for related multisite phosphorylation, where one phosphorylated residue may serve as a priming site for a second modification to occur.

An appropriate foreground for Motif-X was created that preserved multiple phosphorylation information. Using all peptides with 2, 3 or 4 phosphorylations, we centered on each of those sites, and created new amino acid notations for the additional phosphorylated sites that were observed outside the central position. Two different data sets were used as backgrounds (see Example 1 for details).

In both cases we obtained a similar subset of motifs. Twenty significant double-phosphorylation motifs at a minimum of 20 occurrences for pSer and 2 motifs with more than 4 instances for pThr were found (FIG. 6 panels E-H and Table 2).

In general, double phosphorylations were found more frequently in the context of acidic and proline-directed motifs than in a basic environment. Some of the double-phosphorylation motifs identified could be deconvoluted into two separate motifs. For example the acidic motifs, ssxEE and sxsExE can be both decomposed into two sxxE.

Phosphorylation is known to often proceed in a step-wise fashion, where the first event serves as a priming event for the second. Well-known examples of priming phosphorylation motifs were found. For example GSK-3 kinase, whose motif requires a phosphorylated serine at position +4 (sxxxs), was found with 46 occurrences. We found several cases in which only one of the two specific loci in a double-phosphorylation motif was also identified a singly-phosphorylated species, which is suggestive of ordered phosphorylation.

As an example from the double-phosphorylation motif sPxxsP (37 matches), only the single-phosphorylation motif SPxxsP was observed with significance suggesting the phosphorylation of the downstream serine is a priming event for the upstream serine at −4. Other doubly-phosphorylated motifs were more frequent than their singly-phosphorylated counterparts: sPsP was found with 23 occurrences, whereas only 6 and 12 examples were found for SPsP and sPSP, respectively. SPsP has been described previously as a motif for KIS kinase (Manceau et al., 2006). A known KIS substrate, SF1, was found among the 23 phosphopeptides containing this motif.

Example 8

Evaluation of Multiple Motif Relationships within a Single Protein Sequence

Multiple phosphorylation can be further extended to a more complex set of elements than sites within close proximity. A view from the minimal recognition subunit (i.e., motif) perspective can describe trends in multiple phosphorylation regulation. Therefore, motif-motif relationships and explorations of possible patterns of coordinated modifications have the potential to provide insights into kinase crosstalk mechanisms, phosphorylation-dependent protein-protein binding and mechanisms by which two independent phosphorylations dictate different cellular localizations of a protein.

In order to connect multiple intra-protein phosphorylation events from a motif point of view, phosphorylation motifs were correlated within the same protein in a binary fashion, which is described herein by the term "metamotifs." Each phosphorylation site in the data set was assigned to only one motif, prioritizing motifs on the basis of their significance in Table 2. Frequency of co-occurrence was measured as a percentage such that the value reported was the percentage of sites for motif M1 that were found in presence of motif M2. By combining all motifs, a motif-motif matrix can be constructed.

Because peptides and not whole proteins are analyzed, there is a disconnect such that any two phosphorylation events for a given protein may or may not co-exist within the same protein molecule. The only case where one knows that both events co-occur is when both are detected on the same sequenced phosphopeptide.

Figure 7:
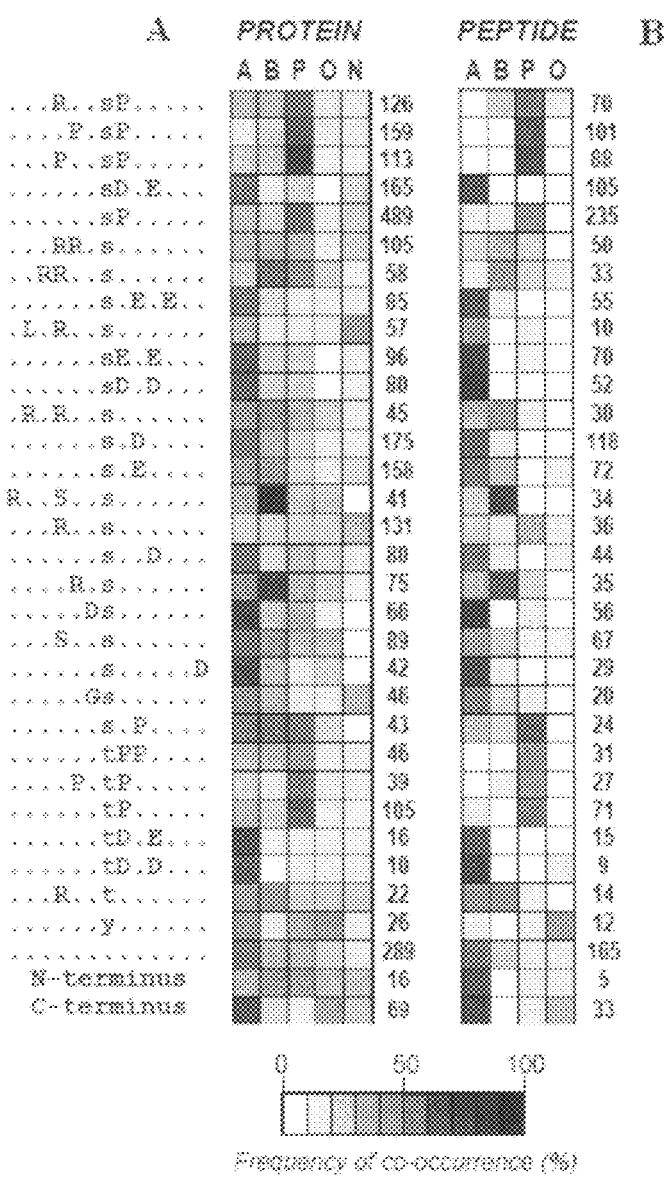
FIG. 7 is a set of charts showing binary motif correlation in multiply-phosphorylated proteins, showing the number of sites for motif M1 that were found in the presence of M2 within the same protein. Frequencies were then normalized to the total number of occurrences of M1. The frequency of each specific motif is shown in the margin.

Therefore, we performed the multisite phosphorylation motif analysis first at the level of multiply phosphorylated proteins (protein level—FIG. 7) and then at a more restricted level where only proteins for which peptides containing 2 or more phosphorylation events were used (peptide level—FIG. 7).

To simplify the metamotif concept and use better defined motifs without diluting the number of occurrences into many motif-motif cells, specific motifs discovered in Table 2 were correlated for co-occurrence with general sequence classes already discussed: acidic (A), basic (B), Pro-directed (P), others (O) or none (N) when the phosphorylation site contained within that motif was the only one detected for that protein (FIG. 7). The metamotif analysis within the same protein (protein level) or within the same peptide (peptide level) often showed similar trends.

In addition to correlating each specific motif (e.g., RxxsP, tPP) for co-occurrence with general motifs (e.g., acidic, basic) as shown in FIG. 7, a full matrix of co-occurrence was constructed using only specific motifs (FIG. 10). This provides the frequency of finding any two examples of specific motifs phosphorylated within the same protein.

From data shown in FIG. 7 and FIG. 10, a number of different phosphorylation trends are found. First, there was a greater frequency of multiple phosphorylation on the exact same motif, such as two different "sP" sequences. In addition, detection of one specific proline-directed motif (e.g., PxtP) was commonly localized with another proline-directed specific motif (e.g., sP) (FIG. 10). In the simplified metamotif analysis, multiple phosphorylation was very likely to occur at two specific motifs of the same general class. This was the case for nearly all the proline-directed motifs and most of the acidic motifs. However, no difference in frequency was observed for the majority of the basic motifs in terms of an additional phosphorylation. This suggests that multiple phosphorylation events are often by the same kinase or similar kinases.

Second, there were motifs that tended to be found in proteins detected only as singly-phosphorylated, for example, CaM kinase family motifs (LxRxxs). These proteins may have more straightforward kinase regulation. Third, several specific motifs (e.g., sxP, Sxxs, Gs, etc) that would not be classified into any of the three general sequence categories were associated equally well with acidic, basic, and proline-directed sequences.

Example 9

Identification of Phosphorylation Sites and Phosphorylated Peptides

A combination of procedures for obtaining a large phosphorylation data set from mouse liver is provided, with a defined error rate in phosphopeptide identification and probability assessment for correct site localization. A data set was used to study phosphorylation at different levels. First, considering the immediate neighboring residues, phosphorylation sites that fit into kinase motifs were found. Second, motifs containing more than one phosphorylated residue were identified. Finally, binary motif relationships were established to understand general trends in multiple phosphorylation by the development of a novel approach that can be extended to correlate other post-translational modifications.

C-terminal phosphorylation was found to be more frequent than at any other location, and distribution of potential kinases for these sites was unique. In addition, double phosphorylation motifs which may be involved in ordered phosphorylation were identified.

Tissue Preparation

A 21-day old Swiss Webster mouse was obtained from Taconic (Germantown, N.Y.). Liver was dissected and dounce homogenized in lysis buffer [50 mM Tris, 75 mM NaCl, 8 M urea (pH 8.1), 10 mM sodium pyrophosphate, 1 mM sodium fluoride, 1 mM β-glycerophosphate, 1 mM sodium orthovanadate and 1 tablet complete Mini protease inhibitor cocktail (Roche) per 10 mL] and further lysed by sonication. The sample was transferred to centrifuge tubes and clarified by centrifugation at 13,000 rpm in a Sorvall SS34 rotor at 4° C. for 15 min. Supernatant was separated into a new tube and protein concentration was measured.

In-Solution Trypsin Digestion

Reduction and alkylation of cysteines were performed on 10 mg of liver protein by incubation in 2.5 mM DTT for 25 min at 60° C. and then 30 min at room temperature in 7 mM iodoacetamide in the dark. The alkylation reaction was quenched by the addition of DTT to 2.5 mM and additional 15 min incubation. Lysate was 8-fold diluted (25 mM Tris, pH 8.1, 1 mM CaCl2), and 40 µg of sequencing grade trypsin (Promega, Madison) were added (5 ng/µL trypsin; enzyme/substrate ratio of 1/225). Digestion was stopped after 15 hours at 37° C. by the addition of TFA to 0.4%, and the pH was verified at ~2. The digest was centrifuged at 3200 rpm to remove insoluble material and then loaded onto a 500 mg tC18 SepPak cartridge (Waters, Milford, Mass.) for peptide desalting. Eluted peptides were lyophilized and stored at −20° C.

SCX Chromatography

Peptides were re-dissolved in 800 µL SCX buffer A (5 mM KH2PO4, pH 2.65, 30% acetonitrile). Preparative separations were carried out on a 9.4 mm×200 mm column, packed with Polysulfoethyl Aspartamide (PolyLC, Columbia, Md.) material (5 µm particle size, 200 Å pore), using a Surveyor pump operating at 2 mL/min and a PDA detector (Thermo Electron, San Jose, Calif.). Two different injections and separations of 400 µL (~5 mg) were performed to avoid column overloading. Three minutes of isocratic buffer A were followed by a linear gradient from 0 to 21% buffer B (5 mM KH2PO4, pH 2.65, 30% acetonitrile, 350 mM KCl) over 35 min, and then several washing steps with 100% buffer B and 100% buffer C (20 mM Tris, pH 8.5). A total of 15 fractions (~3 minute intervals) were collected across each run and identical fraction numbers were pooled. Solvent was removed by lyophilization, and all samples were desalted in 100 mg tC18 SepPak cartridges (Waters, Milford, Mass.). Eluted peptides were lyophilized and stored at −20° C.

Immobilized Metal-Affinity Chromatography (IMAC)

Phosphopeptides were further enriched by IMAC. Each sample was dissolved in 100 µL 250 mM acetic acid, 30% acetonitrile and added to 10 µL of beads (Phos-Select iron affinity gel, Sigma), previously washed 3× with the same buffer. After 60 min incubation at room temperature with vigorous shaking, supernatant was removed, and the resin was washed 3× with 200 µL 250 mM acetic acid, 30% acetonitrile. Phosphopeptides were eluted with 70 µL of 50 mM Tris/NH3, pH 10.0, three times. Eluates were collected in tubes containing 20 µL 10% formic acid. All samples were dried by vacuum centrifugation and afterwards desalted with C18 Empore Disks (3M, Minneapolis, Minn.) (Rappsilber et al., 2003).

MS and MS/MS Analyses

Phosphopeptide enriched mixtures were re-dissolved in 6 µL 5% acetonitrile, 3% formic acid and 3 µL were loaded (15 min) by a Famos autosampler (LC Packings, San Francisco, Calif.) onto a hand-pulled fused silica microcapillary (125 µm×18 cm) column packed with C18 reverse-phase material (Magic C18AQ, 5 µm particles, 200 Å pore size, Michrom Bioresources, Auburn, Calif.). Peptides were separated using an Agilent 1100 series binary pump with in-line flow splitter across a 35 min linear gradient ranging from 6 to 28% acetonitrile in 0.125% formic acid and analyzed in a hybrid linear ion trap—7 Tesla Fourier transform ion cyclotron resonance instrument (LTQ FT, Thermo Electron, San Jose, Calif.). For each cycle, one full MS scan [375-1800 m/z; acquired in the ICR cell at 105 resolution setting and automatic gain control (AGC) target of 106] was followed by 10 data-dependent MS/MS spectra (AGC target 4000, threshold 1800) in the linear ion trap from the 10 most abundant ions (Haas et al., 2006). Selected ions were dynamically excluded for 30 s. Charge-state screening was employed to reject singly-charged ions.

Database Searching and Data-Filtering

To access MS and MS/MS data, .RAW files were converted to the OpenRaw format using the program xr2 or. An in-house perl script was used to extract precursor charge-state and monoisotopic masses from isotopic envelopes. MS/MS spectra were searched using the Sequest algorithm (v.27, rev.12) on a 19 node linux cluster against a composite database containing the mouse IPI protein database (v.3.13, downloaded Dec. 8, 2005 and containing 50,489 sequence entries) and its reversed complement. Search parameters included partially-tryptic specificity, a mass tolerance of ±150 ppm, a static modification of 57.02146 Da (carboxyamidomethylation) on cysteine, and dynamic modifications of 79.96633 Da (phosphorylation) on serine, threonine and tyrosine, and 15.99491 Da (oxidation) on methionine. Additional searches were performed to identify phosphorylation sites contained within the N-terminal peptide from a protein. This included considering each protein's N terminus as acetylated (+42.01056) and allowing for optional cleavage of the initial methionine residue, and to verify that no sites were lost due to incorrect assignment of the monoisotopic peak from the precursor ion (fully-tryptic searches and 1.1 Da tolerance).

Results were first filtered to contain only fully-tryptic peptides, and then other cutoffs were established to achieve maximum sensitivity levels while maintaining <0.1% falsepositives (one reversed sequence hit for every 1000 forward sequence hits). Powerful sample-specific filters for solution charge state and mass accuracy were used (Beausoleil et al., 2006; Haas et al., 2006). A ±3 S.D. mass tolerance window (approximately ±12 ppm) was applied separately to each of the 15 analyses. Following filtering by tryptic state, solution charge, and mass accuracy, only minimal filtering with Sequest scoring (XCorr and dCn') values at the level of the entire data set was then required to achieve <0.1% FP rate. We define the dCn' score as the dCn score to the first non-identical sequence for a match.

The final list of phosphopeptides contained 8,529 entries with 13,560 detected phosphorylation sites. Only two entries corresponded to reverse-sequence matches. These two known falsepositives were removed, and the FP rate was estimated to be 2/8,527 or 0.02% (Elias et al., 2005). The average absolute mass deviation was found to be <10 ppm for the 8,527 phosphopeptides.

Phosphorylation Site Localization

An ambiguity score (Ascore), directly reflecting the probability of correct site assignment, was automatically calculated for every site using in-house software described in Beausoleil et al., 2006. An automated approach to identify the most likely phosphorylation site location included (i) determining the most likely phosphorylation sites candidates, and (ii) calculating the probability of correct phosphorylation site location based only on the likelihood of identifying site-determining ions compared to random chance. The MS/MS spectrum for a candidate phosphopeptide containing multiple possibilities for phosphorylation site location was first separated into windows of 100 m/z units. Within each window, only the top i peaks were retained by intensity, where i represented the peak depth. Predicted b- and y-type ions for each possibility were then overlaid with the processed spectrum. The cumulative binomial probability P was calculated using the number of trials N, the number of successes n, and the probability of success p as follows:

$$P(X) = \sum_{k=n}^{N} \binom{N}{k} p^k (1-p)^{N-k}$$

where P represents the probability of randomly matching at least the given number of fragment ions to the MS/MS spectrum. The total number of trials (N) equaled the total number of fragment ions for the given peptide. The total number of successes (n) equaled the number of ions matched to the spectrum. Within a given window, the probability of matching a peak (p) was equal to i/100. A human readable score was calculated by multiplying −10 by the log(P). This entire process was repeated for i+1, while i<10. A weighed average of all ten scores was called the peptide score. For precise phosphorylation site assignment, the cumulative binomial probability of identifying site-determining b- and y-type ions was calculated for the two highest scoring site locations. The cumulative binomial probability for matching only the site determining ions was calculated using this method with one exception: the total number of trials N was equal to the total number of site determining ions. The probabilities for the two top candidates were converted into human readable scores and subtracted from each other. The resultant score is a metric that measures the likelihood of matching a difference of at least the number of matched site-determining ions by chance from the top two candidates sites and has been termed the ambiguity score (Ascore). An Ascore of 20 (P=0.01) should result in the site being localized with 99% certainty.

A mass window setting of 100 in/z units and a fragment ion tolerance of ±0.3 m/z units were used. Ascores >19 (P<0.01) were considered to be confidently localized. For peptides with Ascores <19, we were careful to never allow an ambiguous site to count for more than one site, regardless of the number of MS/MS spectra or potential site localizations for this peptide. A conservative approach as well was applied when counting the number of phosphopeptides such that different charge states, oxidized methionines, miscleaved versions and ragged ends did not add identifications to our non-redundant numbers.

Gene Ontology Annotations

A database of gene ontology annotations was downloaded from EBI website. Only those categories, for which 50 or more phosphorylation sites were identified, were considered for our analysis.

Classification into General Motif Classes or Sequence Categories

Centered 13-mer sequences were assigned to a motif class sequentially, following a binary decision tree as follows: P at +1 (Pro-directed: P), more than 5 E/D at +1 to +6 (acidic: A), R/K at −3 (basic: B), D/E at +1/+2 or +3 (A), 2 or more R/K at −6 to −1 (B), otherwise (others: O). We excluded tyrosine residues for the background distributions in FIG. 5A due to their relatively low representation in our data set (1%). Phosphotyrosine-containing peptides were classified into the "others" category.

Motif Notation

In this study, we annotated motifs based on the following scheme. Phosphorylated residues were denoted by lowercase letters while non-phosphorylated residues were uppercase. If two residues were significant in the same position then brackets were used (e.g., sxx[DE]). Finally, variable or non-significant positions were denoted by either a "." or lowercase "x".

Motif Analysis

Phosphopeptide sequences were submitted to the Motif-X algorithm (Schwartz and Gygi, 2005) for the identification and discovery of known and novel phosphorylation motifs present in our data set. The motif-building strategy was carried out by finding successive significant residue/position pairs. A binomial distributed model was used as shown below:

$$P(m, c_{xj}, p_{xj}) = \sum_{i=cxj}^{m} \binom{m}{i} p_{xj}^i (1-p_{xj})^{m-i}$$

Where m equaled the number of sequences in the data set matrix, $c_{xj}$ equaled the count of residue x at position j in the data set matrix, and $p_{xj}$ equaled the fractional percentage of residue x at position j in the current background matrix. The result was calculated using the pbinom function in the Math: CDF PERL module on a Linus workstation (2.2 gigahertz microprocessor with 1.5 gigabitz RAM). The statistical significance of each motif extracted, heuristic scores for the motifs were calculated as the sum of the negative log of the binomial probabilities used to generate the motifs:

Score(motif)=Σ−log($P_{binomial}$)

The Mouse IPI database was used as a background. Sequences were centered on each phosphorylation site and extended to 13 amino acids (±6 residues). Only those sites with Ascore >19 were used. Sites which could not be extended because of N or C termini were excluded by the Motif-X algorithm. The significance threshold was set to P<10-6. The minimum number of motif occurrences was set to 1.8% of the entire number of phosphorylations found for each residue (e.g., 50 serines).

For the motifs containing more than one phosphorylation site, multiple phosphorylated peptides were centered on each of the sites and extended to 13 amino acids and used as foreground. Other phosphorylation sites contained within the 13-mers were denoted as B, X or Z for Ser, Thr and Tyr respectively. Only peptides with all the Ascore values >19 for all the sites were considered for this analysis. Two different sets were used as background. A singly-phosphorylated background was created with singly phosphorylated peptides from our data set, which were centered on every nonphosphorylated Ser, Thr and Tyr, maintaining as before B, X, Z phosphorylated residues. Although reduced in size, it had the advantage of defining phosphorylated residues outside the central position residues with the new notations. A total of 1282 (1119, Ser, 155 Thr and 8 Tyr) centered peptides were used as a foreground against a 3293 (1956 Ser, 983 Thr, 352 Tyr) member background. The second was a database background which was the same as for the regular Motif-X analysis, which did not result in any additional motifs being identified (data not shown). Sequence logos were generated with Weblogo (Crooks et al., 2004).

Motif-Motif Correlations (Metamotifs)

In order to construct a matrix that describes the co-occurrence of one motif with another from the same protein, the number of sites for motif M1 that were found in the presence of M2 within the same protein was calculated. Frequencies were then normalized to the total number of occurrences of M1. This was done by considering all specific motifs found and comparing their co-occurrences with each general sequence category (Acidic, Basic, Pro-directed, and Other). For example, for specific motif M1=RxxsP, 126 occurrences were found. For M2=Acidic, 38 occurrences were found in proteins containing RxxsP, such that the likelihood of detecting a phosphorylation event with an acidic motif given the known detection of RxxsP within a single protein was 38/126 or 30%.

For FIG. 10, the same analysis as in FIG. 7 was performed, but both dimensions (M1 and M2) used specific motifs.

Because it was not known whether multiple phosphorylation sites within the same protein were actually co-existing on the same protein molecule, two more analyses were performed exactly as described above but measuring co-occurrence where only phosphopeptides containing multiple phosphorylation sites were used. For these phosphopeptides it was known that both phosphorylation sites and by analogy both motifs were co-existing within the same protein molecule. These matrices are labeled "peptide level" in FIG. 7, FIG. 10.

Example 10

Production of Antibodies of the Invention

Antibodies (Abs) can be produced by a variety of techniques, including conventional antibody methodology e.g., the standard somatic cell hybridization technique of Kohler and Milstein, 1975 Nature 256: 495. Many techniques for producing antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known.

Generation of Antibodies Against Phosphopeptide

Purified phosphopeptide is used as the antigen. To generate antibodies to the phosphopeptides, mice are immunized with purified phosphopeptides as antigens. General immunization schemes for HuMab mice are described in Lonberg, N. et al., 1994 Nature 368(6474): 856-859; Fishwild, D. et al., 1996 Nature Biotechnology 14:845-851 and PCT Publication WO 98/24884. The mice are 6-16 weeks of age upon the first infusion of antigen. A purified preparation (5-50 µg) of phosphopeptide antigen is used to immunize the HuMab mice and KM mice intraperitonealy, subcutaneously (Sc) or by footpad injection.

Mice are immunized twice with antigen in complete Freund's adjuvant or Ribi adjuvant either intraperitonealy (IP), subcutaneously (Sc) or by footpad (FP), followed by 3-21 days IP, Sc or FP immunization (up to a total of 11 immunizations) with the antigen in incomplete Freund's or Ribi adjuvant. The immune response is monitored by retroorbital bleeds. The plasma is screened by ELISA, and mice with sufficient titers of anti-phosphopeptide immunogolobulin are used for fusions. Mice are boosted intravenously with antigen 3 and 2 days before sacrifice and removal of the spleen. Typically, 10-35 fusions for each antigen are performed. Several dozen mice are immunized for each antigen.

To select mice producing antibodies that bound the phosphopeptide, sera from immunized mice can be tested by ELISA as described by Fishwild, D. et al., 1996. Briefly, microtiter plates are coated with purified phosphopeptides at 1-2 µg/ml in PBS, 50 µl/wells incubated 4° C. overnight then blocked with 200 µl/well of 5% chicken serum in PBS/Tween (0.05%). Dilutions of plasma from phosphopeptide-immunized mice are added to each well and incubated for 1-2 hours at ambient temperature. The plates are washed with PBS/Tween and then incubated with a goat-anti-mouse IgG Fc polyclonal antibody conjugated with horseradish peroxidase (HRP) for 1 hour at room temperature. After washing, the plates are developed with ABTS substrate (Sigma, A-1888, 0.22 mg/ml) and analyzed by spectrophotometer at OD 415-495. Mice that developed the highest titers of anti-phosphopeptide antibodies are used for fusions. Fusions are performed and hybridoma supernatants are tested for anti-phosphopeptide activity by ELISA.

The mouse splenocytes, isolated from the mice, are fused with PEG to a mouse myeloma cell line based upon standard protocols. The resulting hybridomas are then screened for the production of antigen-specific antibodies. Single cell suspensions of splenic lymphocytes from immunized mice are fused to one-fourth the number of SP2/0 nonsecreting mouse myeloma cells (ATCC, CRL 1581) with 50% PEG (Sigma). Cells are plated at approximately $1 \times 10^5$/well in flat bottom microtiter plate, followed by about two week incubation in selective medium containing 10% fetal bovine serum, 10% P388D 1 (ATCC, CRL TIB-63) conditioned medium, 3-5% origen (IGEN) in DMEM (Mediatech, CRL 10013, with high glucose, L-glutamine and sodium pyruvate) plus 5 mM HEPES, 0.055 mM 2-mercaptoethanol, 50 mg/lnni gentamycin and 1×HAT (Sigma, CRL P-7185). After 1-2 weeks, cells are cultured in medium in which the HAT is replaced with HT. Individual wells are then screened by ELISA for anti-phosphopeptide IgG antibodies. Once extensive hybridoma growth occurred, medium is monitored usually after 10-14 days. The antibody secreting hybridomas are replated, screened again and, if still positive for IgG, anti-phosphopeptide antibodies are subcloned at least twice by limiting dilution. The stable subclones are then cultured in vitro to generate small amounts of antibody in tissue culture medium for further characterization.

Immunization of Ig Mice

When Ig mice are used to raise antibodies of the invention, such mice can be immunized with a purified or enriched preparation of phosphopeptide antigen as described by Lonberg, N. et al., 1994 Nature 368(6474): 856-859; Fishwild, D. et al., 1996 Nature Biotechnology 14: 845-851; and PCT Publication. WO 98124884 and WO 01/14424. The mice can be 6-16 weeks of age upon the first infusion. For example, a purified or recombinant preparation (5-50 µg) of phosphopeptide antigen can be used to immunize the human Ig mice intraperitoneally.

Detailed procedures to generate antibodies to the phosphopeptides are described above. Cumulative experience with various antigens has shown that the transgenic mice respond when initially immunized intraperitoneally (IP) with antigen in complete Freund's adjuvant, followed by every other week IP immunizations (up to a total of 6) with antigen in incomplete Freund's adjuvant. However, adjuvants other than Freund's are also found to be effective. In addition, whole cells in the absence of adjuvant are found to be highly immunogenic. The immune response can be monitored over the course of the immunization protocol with plasma samples being obtained by retroorbital bleeds. The plasma can be screened by ELISA, and mice with sufficient titers of anti-phosphopeptide immunoglobulin can be used for fusions. Mice can be boosted intravenously with antigen 3 days before sacrifice and removal of the spleen. It is expected that 2-3 fusions for each immunization may need to be performed. Between 6 and 24 mice are typically immunized for each antigen.

Generation of Hybridomas Producing Antibodies

To generate hybridomas producing antibodies of the invention, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to one-sixth the number of P3×63-Ag8.653 nonsecreting mouse myeloma cells (ATCC, CRL 1580) with 50% PEG. Cells are plated at approximately 2×145 in flat bottom microtiter plates, followed by a two week incubation in selective medium containing 20% fetal Clone Serum, 18% "653" conditioned media, 5% origen (IGEN), 4 mM L-glutamine, 1 mM sodium pyruvate, 5 mM HEPES, 0:055 mM 2-mercaptoethanol, 50 units/ml penicillin, 50 mg/ml streptomycin, 50 mg/ml gentamycin and 1×HAT (Sigma; the HAT is added 24 hours after the fusion). After approximately two weeks, cells can be cultured in medium in which the HAT is replaced with HT. Individual wells can then be screened by ELISA for IgM and IgG antibodies. Once extensive hybridoma growth occurs, medium can be observed usually after 10-14 days. The antibody secreting hybridomas can be replated, screened again, and if still positive for IgG, the antibodies can be subcloned at least twice by limiting dilution. The stable subclones can then be cultured in vitro to generate small amounts of antibody in tissue culture medium for characterization.

To purify antibodies, selected hybridomas can be grown in two-liter spinner-flasks for antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by $OD_{280}$ using 1.43 extinction coefficient. The antibodies can be aliquoted and stored at −80° C.

Example 11

Quantitative Analysis of Binding Affinities: Affinity Determination

In order to further characterize the anti-phosphopeptide antibodies, the affinity to the mouse phosphopeptide is determined. The phosphopeptides are immobilized on a CM5 Biacore chip and the Fabs are applied in the mobile phase in different concentrations. For a reliable determination of monovalent affinities only such Fab batches were used for Biacore measurements which showed ≥90% monomeric fraction in a size exclusion chromatography. All tested Fabs are found to have affinity to the mouse phosphopeptides below 100 nM.

What is claimed is:

1. A method of identifying phosphorylation sites within a plurality of proteins or peptides or mixture thereof comprising:

subjecting the protein or peptide to phosphate enrichment and analyzing the phosphate enriched protein or peptide using microcapillary liquid chromatography coupled online to a tandem mass spectrometer (LC-MS/MS) to produce a raw data set of spectra comprising amino acids and applying at least one filtering criterion to the raw data set of spectra to obtain a refined data set of spectra;

comparing the refined data set of spectra to a protein database of amino acid sequences in a forward direction of the sequences, to identify at least one phosphorylated amino acid residue in each of the phosphorylation sites within the sequences;

evaluating correct location of the phosphorylation sites by determining site-determining ions and computing the likelihood of detection in the refined data set of spectra by chance alone, wherein the site-determining ions comprise ions whose detection distinguishes between at least two adjacent acceptor residues, wherein the residues are at least one selected from the group of: serine, threonine, and tyrosine, wherein computing the likelihood of detection comprises identifying absence or presence of the site-determining b- and y-type fragment ions in the refined data set of spectra using an algorithm, wherein the algorithm comprises a cumulative binomial probability P calculated using number of trials N, number of successes n, and probability of success p:

$$P(X) = \sum_{k=n}^{N} \binom{N}{k} p^k (1-p)^{N-k}$$

such that P represents the probability of randomly matching at least a given number of fragment ions to the spectra, the total number of trials (N) equals total number of the fragment ions for the protein or peptide, and the total number of successes (n) equaled the number of ions matched to the refined data set of spectra, and such that identifying further includes multiplying −10 by the log(P)

and;

comparing the intrinsic amino acid sequence alignment of phospho-residues to a dynamic statistical background to extract phosphorylation motifs from the phosphorylation sites, wherein comparing comprises using the phosphorylation sites having an Ascore of more than 19, and correlating the phosphorylation motifs with cellular localization and protein function, thereby identifying phosphorylation sites.

2. The method according to claim 1, wherein prior to identifying, the method further comprises comparing the refined amino acid sequence data set of spectra to the protein database of amino acid sequences in a reverse direction of the sequences, to calculate a false positive rate wherein the false positive rate is used to remove redundant spectra of amino acid sequences from the refined data set.

3. The method according to claim 1, wherein prior to subjecting the plurality of proteins or peptides or mixture thereof to phosphate enrichment, the proteins or peptides or mixture thereof are digested with trypsin.

4. The method according to claim 1, wherein subjecting to the phosphate enrichment further comprises a chemical strategy selected from the group of: beta-elimination; phosphoramidate chemistry; peptide immunopreciptation with phospho-specific motif antibodies; affinity purification through metal complexation with the phosphate group; solution charge-based enrichment by cation exchange chromatography; immobilized metal ion affinity chromatography; and combinations thereof.

5. The method according to claim 1, wherein subjecting to the phosphate enrichment further comprises cation exchange chromatography and immobilized metal ion affinity chromatography.

6. The method according to claim 1, wherein the tandem mass spectrometer (LC-MS/MS) to produce a raw data set of spectra a further comprises a hybrid linear ion trap/Fourier transform ion cyclotron resonance (FTICR) mass spectrometer, and spectra were generated by collision-activated dissociation (CAD) in a linear ion trap.

7. The method according to claim 1, wherein identifying the phosphorylation sites further comprises analyzing a position of a phosphorylation site along the protein sequence by dividing the protein length into 1% bins and counting the number of sites within each division.

8. The method according to claim 7, further comprising observing an enrichment of phosphorylation sites in the C-terminal-most bin compared to bins located at the N-terminal and along the length of the protein.

9. The method according to claim 1, further comprising observing the motif classes, wherein motif classes are selected from the group of: proline directed, acidic, basic, and motifs not yet associated with a particular kinase.

10. The method according to claim 9, further comprising identifying phosphopeptides having at least two phosphorylation sites.

11. The method according to claim 10, further comprising measuring frequency of co-occurrence for phosphorylation motifs within phosphopeptides.

12. The method according to claim 10, wherein the phosphorylation sites and phosphopeptides are identified within an amino acid sequence of a lipolysis-stimulated receptor protein.

13. The method according to claim 1, further comprising an additional step of generating an antibody by immunizing a subject with a purified phosphopeptide as an antigen.

14. The method according to claim 13, wherein the resulting antibody binds the phosphorylation site within the protein or peptide.

15. The method according to claim 13, wherein the antibody is immobilized to a discrete and known spot on a substrate surface.

16. The method according to claim 1, wherein identifying ambiguous phosphorylation sites comprises identifying site-determining b- and y-type fragment ions.

17. The method according to claim 1, wherein near certain probability (P<0.01) of correct localization corresponds to an Ascore score of more than about 19.

18. The method according to claim 1, wherein applying at least one filtering criterion comprises filtering by at least one selected from the group of: tryptic state, solution charge, mass accuracy or Sequest scoring values.

19. The method according to claim 1, wherein applying at least one filtering criterion is used to achieve false positive rate of less than about 0.1%.

* * * * *